(12) United States Patent
Lopez-Tapia et al.

(10) Patent No.: US 6,335,459 B1
(45) Date of Patent: Jan. 1, 2002

(54) ARYL CARBOXYLIC ACID AND ARYL TETRAZOLE DERIVATIVES AS IP RECEPTOR MODULATORS

(75) Inventors: Francisco Javier Lopez-Tapia, Union City; Alexander Victor Muehldorf; Counde O'Yang, both of Sunnyvale; Daniel Lee Severance, San Diego, all of CA (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 09/456,167

(22) Filed: Dec. 7, 1999

Related U.S. Application Data

(60) Provisional application No. 60/113,446, filed on Dec. 23, 1998, and provisional application No. 60/151,814, filed on Aug. 30, 1999.

(51) Int. Cl.$^7$ ............................................. C07C 261/00
(52) U.S. Cl. ........................... 560/27; 560/32; 560/125; 560/163; 548/251; 548/252; 548/253; 514/381
(58) Field of Search ............................ 560/27, 32, 125; 560/163; 514/381

(56) References Cited

U.S. PATENT DOCUMENTS

| | | |
|---|---|---|
| 3,649,637 A | 3/1972 | Howes et al. |
| 4,878,942 A | 11/1989 | Motegi et al. |
| 5,084,466 A | 1/1992 | Alig et al. |
| 5,753,700 A | 5/1998 | Nagao et al. |
| 5,763,489 A | 6/1998 | Taniguchi et al. |
| 5,972,965 A | 10/1999 | Taniguchi et al. |
| 6,013,673 A | 1/2000 | Nagao et al. |
| 6,018,068 A | 1/2000 | Nagao et al. |

FOREIGN PATENT DOCUMENTS

| | | |
|---|---|---|
| DE | 2432560 | 1/1976 |
| EP | 558 062 B1 | 7/1997 |
| GB | 1079414 | 8/1967 |
| HU | 217 028 | 11/1999 |
| JP | 58032859 | 8/1981 |
| WO | WO 95/21863 | 8/1995 |
| WO | WO 99/24397 | 5/1999 |
| WO | WO 99/32435 | 7/1999 |

OTHER PUBLICATIONS

Ono, K et al, Tetrahedron Lett (1994) 35(24) 4133–6.*
Vavayannis et al., Eur.J.Med.Chem Chim.Ther, 1985, 20, 37–42.
Marsh et al., J.Chem.Soc.Chem.Commun., 1996, 8, 941–942.
Goodman & Gilman's, *The Pharamcological Basis of Therapeutics*, ninth edition, McGraw–Hill, New York, 1996, Chapter 26:601–616.
Coleman, R.A. *Pharmacological Reviews,* 1994, 46:205–209.
Creager, M.A., *Principles of Internal Medicine*, 1998, 1398–1406.

* cited by examiner

Primary Examiner—Paul J. Killos
(74) Attorney, Agent, or Firm—Janet Kaku

(57) ABSTRACT

This invention relates to compounds which are generally IP receptor modulators, particularly IP receptor agonists, and which are represented by Formula I:

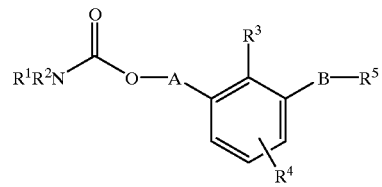

wherein $R^1$, $R^2$, $R^3$, $R^4$, $R^5$, A, and B are as defined in the specification, and individual isomers, racemic or non-racemic mixtures of isomers, and pharmaceutically acceptable salts or solvates thereof. The invention further relates to pharmaceutical compositions containing such compounds and methods for their use as therapeutic agents.

32 Claims, No Drawings

ARYL CARBOXYLIC ACID AND ARYL TETRAZOLE DERIVATIVES AS IP RECEPTOR MODULATORS

CROSS REFERENCE TO RELATED APPLICATIONS

This application claims benefit under Title 35 U.S.C. 119(e) of U.S. Provisional Application Nos. 60/113,446, filed Dec. 23 1998, and 60/151,814, filed Aug. 30, 1999; both applications are incorporated herein by reference.

BACKGROUND OF THE INVENTION

1. Field of the Invention

This invention relates to prostaglandin $I_2$ (IP) receptor modulators, particularly IP receptor agonists, especially certain aryl carboxylic acids and aryl tetrazole derivatives, pharmaceutical compositions containing them, and methods for their use as therapeutic agents.

2. Background of the Invention

Prostacyclin ($PGI_2$) is a member of the prostaglandin family and is the endogenous agonist ligand for the IP receptor. $PGI_2$ exhibits numerous physiological and pharmacological effects throughout the body and has prominent actions on the cardiovascular system, especially blood vessels, various blood cells including platelets, kidneys, autonomic nerves, and components of the inflammatory and immune systems. For example, in the cardiovascular system, $PGI_2$ produces profound vasodilatation resulting ultimately in hypotension. It also acts on non-vascular smooth muscles to cause bronchodilatation, relaxation of the uterus, and contraction of gastrointestinal smooth muscle. In addition, it decreases the pH, pepsin content, and overall secretion of gastric acid. In the blood, $PGI_2$ inhibits the aggregation of platelets and contributes to the anti-thrombogenic properties of the intact vascular wall. The use of stable analog mimics of $PGI_2$ also suggests that it can inhibit platelet deposition on thrombogenic surfaces such as atherosclerotic plaques. In the kidney, $PGI_2$ provokes diuresis, natriuresis, kaliuresis, and causes secretion of renin from the renal cortex.

Due to the lability of $PGI_2$, a variety of chemically unique analogs have been developed, but these lack receptor selectivity and/or are rapidly degraded by biotransformation. Currently, there is a need for potent, well-tolerated, highly selective IP receptor agonists with pharmacokinetics suitable for long-term, convenient (i.e., QD, BID, TID) oral dosing. The compounds of the present invention and compositions containing them address this need and are useful for the treatment of various disorders with fewer side effects.

3. Description of the Related Art

U.S. Pat. No. 3,649,637 (Howes et al.) refers to certain phenoxy tetrazole derivatives which are disclosed as being useful for treating inflammatory disorders.

U.S. Pat. No. 4,878,942 (Motegi et al.) refers to certain benzamide derivatives which are disclosed as having herbicidal and plant growth regulating activity.

U.S. Pat. Nos. 5,378,716, 5,536,736, 5,703,099, 5,935,985 (Hamaka et al.) and European Patent No. EP 558 062 B1 refer to certain phenoxyacetic acid derivatives which are disclosed as having IP receptor inhibitory activity on blood platelet aggregation.

U.S. Pat. No. 5,763,489 (Taniguchi et al.) and PCT Published Application WO 95/24393 refer to certain naphthalene derivatives which are disclosed as having IP receptor agonist activity useful for treating arterial obstruction, restenosis, arteriosclerosis, cerebrovascular disease or ischemic heart disease.

British Patent Application No. GB 1,079,414 (assigned to Smith & Nephew) refers to certain N-phenyl-o-carbamoylphenoxyacetic acid derivatives which are disclosed as having analgesic and anti-inflammatory activity.

German Patent Application No. DT 24 32 560 (assigned to Boehringer Mannheim) refers to certain 2-(4-carbaniloylalkyl)phenoxy alkanoic acid derivatives which are disclosed as being useful for treating atherosclerosis and as intermediates for antibiotics with β-lactam structure.

PCT Published Application WO 99/24397 (assigned to Fujisawa) refers to certain benzocycloheptene derivatives which are disclosed as having IP receptor agonist activity useful for treating arterial obstruction, cerebrovascular disease, hepatic cirrhosis, arteriosclerosis, ischemic heart disease, restenosis after percutaneous transluminal coronary angioplasty, hypertension, and dermatosis.

PCT Published Application WO 99/32435 (assigned to Fujisawa) refers to certain naphthalene derivatives which are disclosed as having IP receptor agonist activity useful for treating arteriosclerosis, cerebrovascular disease, ischemic heart disease, dermatosis, inflammatory bowel disease, and for inhibiting cancer metastasis.

Vavayannis et al., *Eur. J. Med. Chem. Chim. Ther.* 1985, 20, 37–42, refers to certain dimethylcarbamate derivatives which are disclosed as being having anticholinesterase activity.

Marsh et al., *J. Chem. Soc. Chem. Commun.* 1996, 8, 941–942 refers to certain solid phase polyamine linkers which are disclosed as being useful in the synthesis and preparation of directed libraries against trypanothione reductase.

All publications, patents, and patent applications cited herein, whether supra or infra, are each hereby incorporated by reference in their entirety.

SUMMARY OF THE INVENTION

This invention provides compounds of Formula I:

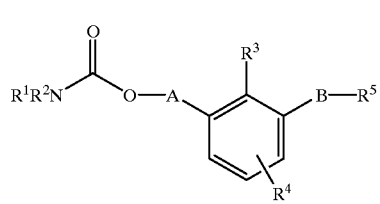

wherein:
- $R^1$ and $R^2$ are each independently in each occurrence alkyl, aryl, aralkyl, heteroaryl, cycloalkyl, or heterocyclyl;
- $R^3$ and $R^4$ are each independently in each occurrence hydrogen, alkyl, alkoxy, amino, halogen, haloalkyl, hydroxyalkyl, nitro, aryl, aralkyl, or heterocyclyl;
- $R^5$ is independently in each occurrence —$COOR^6$ or tetrazolyl;
- $R^6$ is independently in each occurrence hydrogen or alkyl;
- A is independently in each occurrence alkylene or alkenylene;
- B is independently in each occurrence —$O(CH_2)_m$— or —$(CH_2)_n$—;
- m is independently in each occurrence an integer from 1 to 8 inclusive;
- n is independently in each occurrence an integer from 0 to 8 inclusive; or individual isomers, racemic or non-racemic mixtures of isomers, or pharmaceutically acceptable salts or solvates thereof.

This invention further relates to pharmaceutical compositions comprising a therapeutically effective amount of at least one compound of Formula I, or individual isomers, racemic or non-racemic mixtures of isomers, or pharmaceutically acceptable salts or solvates thereof, in admixture with at least one suitable carrier. In a preferred embodiment, the pharmaceutical compositions are suitable for administration to a subject having a disease state that is alleviated by treatment with an IP receptor modulator, particularly an IP receptor agonist.

This invention further relates to pharmaceutical compositions suitable for administration to a subject comprising a therapeutically effective amount of at least one compound of Formula I, or individual isomers, racemic or non-racemic mixtures of isomers, or pharmaceutically acceptable salts or solvates thereof, in admixture with at least one pharmaceutically acceptable carrier.

This invention further relates to methods of treatment comprising administering to a subject in need of such treatment a therapeutically effective amount of at least one compound of Formula I, or individual isomers, racemic or non-racemic mixtures of isomers, or pharmaceutically acceptable salts or solvates thereof. In a preferred embodiment the subject in need of such treatment suffers from a disease state associated with improper wound healing, tissue necrosis, premature uterine contraction, gastric ulceration, sexual dysfunction in males and females, severe menstrual pain, improper immunoregulation, improper platelet aggregation, or improper neutrophil function. In another preferred embodiment the compound of Formula I, or individual isomers, racemic or non-racemic mixtures of isomers, or pharmaceutically acceptable salts or solvates thereof, is an IP receptor modulator, particularly an IP receptor agonist.

This invention further relates to methods of treatment comprising administering to a subject suffering from a disease state associated with improper blood flow, a therapeutically effective amount of at least one compound of Formula I, or individual isomers, racemic or non-racemic mixtures of isomers, or pharmaceutically acceptable salts or solvates thereof. In a preferred embodiment, the subject has a cardiovascular disease state, a hypertensive disease state, an ischemia disease state, or a renal disease state. In a more preferred embodiment, the subject has a cardiovascular disease state which is peripheral arterial occlusive disease (PAOD), intermittent claudication, critical limb ischemia, thrombotic disease, atherosclerosis, thromboangiitis obliterans (Buerger's disease), Raynaud's syndrome, Takayashu's disease, migratory superficial vein thrombophlebitis, acute arterial occlusion, coronary artery disease, restenosis following angioplasty, stroke, or recurrent myocardial infarction. In another preferred embodiment, the compound of Formula I, or individual isomers, racemic or non-racemic mixtures of isomers, or pharmaceutically acceptable salts or solvates thereof, is an IP receptor modulator, particularly an IP receptor agonist.

DETAILED DESCRIPTION OF THE INVENTION

Definitions

Unless otherwise stated, the following terms used in this Application, including the specification and claims, have the definitions given below. It must be noted that, as used in the specification and the appended claims, the singular forms "a," "an" and "the" include plural referents unless the context clearly dictates otherwise.

"Alkyl" means the monovalent branched or unbranched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, butyl, isobutyl, sec-butyl, tert-butyl, pentyl, n-hexyl, octyl, dodecyl, and the like.

"Alkylene" means the divalent linear or branched saturated hydrocarbon radical, consisting solely of carbon and hydrogen atoms, having from one to eight carbon atoms inclusive, unless otherwise indicated. Examples of alkylene radicals include, but are not limited to, methylene, ethylene, trimethylene, propylene, tetramethylene, pentamethylene, ethylethylene, and the like.

"Alkenylene" means the divalent linear or branched unsaturated hydrocarbon radical, containing at least one double bond and having from two to eight carbon atoms inclusive, unless otherwise indicated. The alkenylene radical includes the cis or trans ((E) or (Z)) isomeric groups or mixtures thereof generated by the asymmetric carbons. Examples of alkenylene radicals include, but are not limited to ethenylene, 2-propenylene, 1-propenylene, 2-butenyl, 2-pentenylene, and the like.

"Alkoxy" means the radical —OR wherein R is alkyl as defined herein. Examples of alkoxy radicals include, but are not limited to, methoxy, ethoxy, isopropoxy, butoxy, sec-butoxy, isobutoxy, and the like.

"Aralkyl" means the radical R'R"—wherein R' is an aryl radical as defined herein, and R" is an alkyl radical as defined herein. Examples of aralkyl radicals include, but are not limited to, benzyl, phenylethyl, 3-phenylpropyl, and the like.

"Aryl" means the monovalent monocyclic aromatic hydrocarbon radical consisting of one or more fused rings in which at least one ring is aromatic in nature, which can optionally be substituted with hydroxy, cyano, lower alkyl, lower alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of aryl radicals include, but are not limited to, phenyl, naphthyl, biphenyl, indanyl, anthraquinolyl, and the like.

"Cycloalkyl" means the monovalent saturated carbocyclic radical consisting of one or more rings, which can optionally be substituted with hydroxy, cyano, alkyl, alkoxy, thioalkyl, halogen, haloalkyl, hydroxyalkyl, nitro, alkoxycarbonyl, amino, alkylamino, dialkylamino, aminocarbonyl, carbonylamino, aminosulfonyl, sulfonylamino, and/or trifluoromethyl, unless otherwise indicated. Examples of cycloalkyl radicals include, but are not limited to, cyclopropyl, cyclobutyl, 3-ethylcyclobutyl, cyclopentyl, cyclohexyl, cycloheptyl, and the like.

"Heteroaryl" means the monovalent aromatic carbocyclic radical having one or more rings incorporating one, two, or three heteroatoms within the ring (chosen from nitrogen, oxygen, or sulfur) which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heteroaryl radicals include, but are not limited to, imidazolyl, oxazolyl, pyrazinyl, thiophenyl, quinolyl, benzofuryl, pyridiyl, indolyl, pyrrolyl, pyranyl, naphtyridinyl, and the like.

"Heterocyclyl" means the monovalent saturated carbocyclic radical, consisting of one or more rings, incorporating one, two, or three heteroatoms (chosen from nitrogen, oxygen or sulfur), which can optionally be substituted with hydroxy, cyano, lower alkyl, lower alkoxy, thioalkyl, halo, haloalkyl, hydroxyalkyl, nitro, alkoxycarbonyl, amino, alkylamino, dialkylamino, aminocarbonyl, carbonylamino, aminosulfonyl, sulfonylamino and/or trifluoromethyl, unless otherwise indicated. Examples of heterocyclic radicals include, but are not limited to, morpholinyl, piperazinyl, piperidinyl, pyrrolidinyl, tetrahydropyranyl, thiomorpholinyl, and the like.

"Halogen" means the radical fluoro, bromo, chloro and/or iodo.

"Haloalkyl" means alkyl as defined herein substituted in any position with one or more halogen atoms as defined herein. Examples of haloalkyl radicals include, but are not limited to, 1,2-difluoropropyl, 1,2-dichloropropyl, trifluoromethyl, 2,2,2-trifluoroethyl, 2,2,2-trichloroethyl, and the like.

"Hydroxyalkyl" means alkyl as defined herein, substituted with one or more hydroxy groups. Examples of hydroxyalkyl radicals include, but are not limited to, hydroxymethyl, 2-hydroxyethyl, 2-hydroxypropyl, 3-hydroxypropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl, and 2-(hydroxymethyl)-3-hydroxypropyl, and the like.

"Isomer" means different compounds that have the same molecular formula, but differ in the nature or the sequence of bonding of their atoms or in the arrangement of their atoms in space. Isomers that differ in the arrangement of their atoms in space are termed "stereoisomers". Stereoisomers that are mirror images of each other and optically active are termed "enantiomers", and stereoisomers that are not mirror images of one another are termed "diastereoisomers".

"Chiral isomer" means a compound with one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the *Sequence Rule of Cahn*, Ingold and Prelog (Cahn et al., *Angew. Chem. Inter.* Edit. 1966, 5, 385; errata 511; Cahn et al., *Angew. Chem.* 1966, 78, 413; Cahn and Ingold *J. Chem. Soc.* (London) 1951, 612; Cahn et al., *Experientia* 1956, 12, 81; Cahn, *J. Chem.Educ.* 1964, 41, 116).

"Geometric isomer" means the diastereomers that owe their existence to hindered rotation about double bonds. These configurations are differentiated in their names by the prefixes cis- and trans-, or Z and E, which indicate that the groups are on the same or opposite side of the double bond in the molecule according to the Cahn-Ingold-Prelog rules.

"Atropic isomer" means the isomers owing their existence to restricted rotation caused by hindrance of rotation of large groups about a central bond.

"Leaving group" means the group with the meaning conventionally associated with it in synthetic organic chemistry, i.e., an atom or group displaceable under alkylating conditions. Examples of a leaving group include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Protective group" or "protecting group" has the meaning conventionally associated with it in synthetic organic chemistry, i.e., a group which selectively blocks one reactive site in a multifunctional compound such that a chemical reaction can be carried out selectively at another unprotective reactive site. Certain processes of this invention rely upon the protecting groups to block reactive oxygen atoms present in the reactants. Acceptable protective groups for alcoholic or phenolic hydroxyl groups, which may be removed successively and selectively include groups protected as acetates, haloalkyl carbonates, benzyl ethers, alkylsilyl ethers, heterocyclyl ethers, methyl or other alkyl ethers, and the like. Protective or blocking groups for carboxyl groups are similar to those described for hydroxyl groups, preferably tert-butyl, benzyl, or methyl esters.

"Deprotection" or "deprotecting" is the process by which a protective group is removed after the selective reaction is completed. Certain protective groups may be preferred over others due to their convenience or relative ease of removal. Deprotecting reagents for protected hydroxyl or carboxyl groups include potassium or sodium carbonates, lithium hydroxide in alcoholic solutions, zinc in methanol, acetic acid, trifluoroacetic acid, palladium catalysts, or boron tribromide, and the like.

"Optional" or "optionally" means that the subsequently described event or circumstance may but need not occur, and that the description includes instances where the event or circumstance occurs and instances in which it does not. For example, "optional bond" means that the bond may or may not be present, and that the description includes single, double, or triple bonds.

"Inert organic solvent" or "inert solvent" means a solvent inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable carrier" means a carrier that is useful in preparing a pharmaceutical composition that is generally compatible with the other ingredients of the composition, not deleterious to the recipient, and neither biologically nor otherwise undesirable, and includes a carrier that is acceptable for veterinary use or human pharmaceutical use. "A pharmaceutically acceptable carrier" as used in the specification and claims includes both one and more than one such carrier.

"Pharmaceutically acceptable salt" of a compound means a salt that is pharmaceutically acceptable and that possesses the desired pharmacological activity of the parent compound. Such salts, for example, include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2] oct-2-ene-1-carboxylic acid, glucoheptonic acid, 4,4'-methylenebis-(3-hydroxy-2-ene-1 -carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like;

(2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

"Subject" means mammals and non-mammals. Examples of mammals include, but are not limited to, any member of the Mammalia class: humans, non-human primates such as chimpanzees and other apes and monkey species; farm animals such as cattle, horses, sheep, goats, swine; domestic animals such as rabbits, dogs and cats; laboratory animals including rodents, such as rats, mice, and guinea pigs, and the like. Examples of non-mammals include, but are not limited to birds, and the like. The term does not denote a particular age or sex.

"Treating" or "treatment" of a disease state includes:

(1) preventing the disease state, i.e., causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

"Disease state" means any disease, condition, symptom, or indication.

"Therapeutically effective amount" means the amount of a compound that, when administered to a subject for treating a disease state, is sufficient to effect such treatment for the disease state. The "therapeutically effective amount" will vary depending on the compound, the disease state being treated, the severity of the disease state treated, the age and relative health of the subject, the route and form of administration, the judgement of the attending medical practitioner, and other factors.

"Modulator" means a molecule such as a compound that interacts with a target. The interactions include, but are not limited to, agonist, antagonist, and the like, as defined herein.

"Agonist" means a molecule such as a compound, a drug, an enzyme activator or a hormone that enhances the activity of another molecule or receptor site.

"Antagonist" means a molecule such as a compound, a drug, an enzyme inhibitor, or a hormone, that diminishes or prevents the action of another molecule or receptor site.

"Pharmacological effect" encompasses effects produced in the subject that achieve the intended purpose of a therapy. In a preferred embodiment a pharmacological effect means the treatment of a subject in need of such treatment. For example, a pharmacological effect would be one that results in the prevention, alleviation or reduction of a disease state associated with improper blood flow, improper wound healing, tissue necrosis, premature uterine contraction, gastric ulceration, sexual dysfunction in males and females, alleviation of severe menstrual pain, or improper neutrophil function, in a subject in need of such treatment. In a another preferred embodiment, a pharmacological effect means that the activation of the IP receptors is associated with therapeutic benefit in a subject having a disease state treatable by the administration of an IP receptor modulator, in particular an IP receptor agonist.

Nomenclature

The naming and numbering of the compounds of this invention are illustrated below:

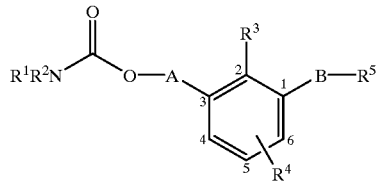

I

In general, the nomenclature used in this Application is based on AutoNom, a Beilstein Institute computerized system for the generation of IUPAC systematic nomenclature. However, because a strict adherence to these recommendations would result in the names changing substantially when only a single substituent is changed, compounds have been named in a form that maintains consistency of nomenclature for the basic structure of the molecule.

For example, a compound of Formula I wherein $R^1$ and $R^2$ are each phenyl, $R^3$ is methyl, $R^4$ is hydrogen, $R^5$ is —COOH, A is methylene, B is —O(CH$_2$)$_m$—, and m is 1, is named {3-[(diphenylcarbamoyloxy)methyl]-2-methylphenoxy} acetic acid.

For example, a compound of Formula I wherein $R^1$ is phenyl, $R^2$ is benzyl, $R^3$ and $R^4$ are each hydrogen, $R^5$ is —COOH, A is propenylene, B is —(CH$_2$)$_n$—, and n is 2, is named 3-{3-[3-(benzylphenylcarbamoyloxy)propenyl]phenyl} propionic acid.

Preferred Compounds

Among the family of compounds of the present invention set forth in the Summary of the Invention, certain compounds of Formula I are preferred wherein:

$R^1$ and $R^2$ are each independently in each occurrence preferably aryl or aralkyl, more preferably phenyl or benzyl, most preferably phenyl.

$R^3$ and $R^4$ are each independently in each occurrence preferably hydrogen, alkyl, aryl, aralkyl, or halogen, more preferably hydrogen, methyl, ethyl, n-propyl, isopropyl, butyl, phenyl, benzyl, bromo, or chloro, most preferably hydrogen or methyl.

$R^5$ is independently in each occurrence preferably —$COOR^6$.

$R^6$ is independently in each occurrence preferably hydrogen or alkyl, more preferably hydrogen.

A is independently in each occurrence preferably alkylene or alkenylene.

B is independently in each occurrence preferably —$O(CH_2)_m$—.

m is independently in each occurrence preferably an integer 1 to 5 inclusive.

n is independently in each occurrence preferably an integer 0 to 5 inclusive.

It is understood that the preferred compounds of Formula I also include the isomers of compounds of Formula I, in particular the cis and trans isomers, or racemic or non-racemic mixtures of isomers, or pharmaceutically acceptable salts of solvates thereof.

Exemplary particularly preferred compounds include the following compounds of Formula I, or individual isomers, racemic or non-racemic mixtures of isomers, or pharmaceutically acceptable salts or solvates thereof:

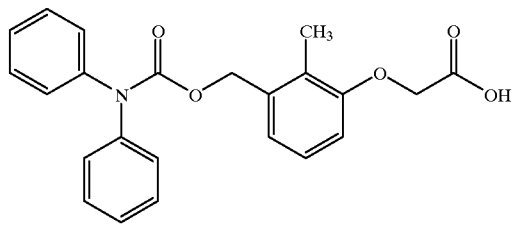

{3-[diphenylcarbamoyloxy)methyl]-2-methylphenoxy}acetic acid;

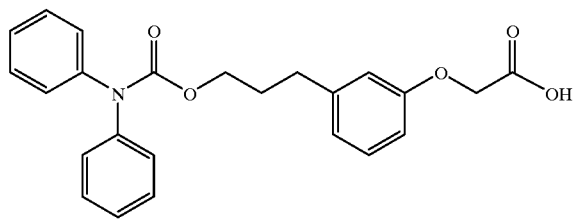

[3-(3-diphenylcarbamoyloxypropyl)phenyl]acetic acid;

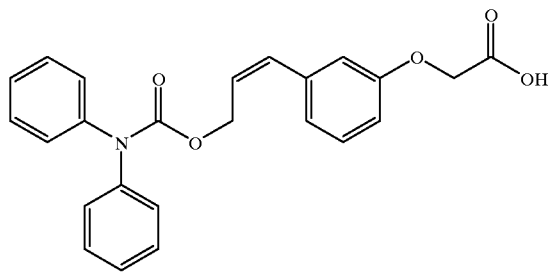

cis-[3-(3-diphenylcarbamoyloxypropenyl)phenoxy]acetic acid;

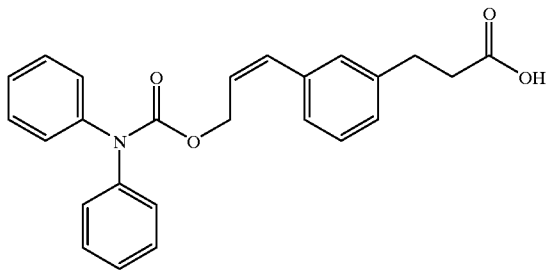

cis-3[3-(3-diphenylcarbamoyloxypropenyl)phenyl]propionic acid;

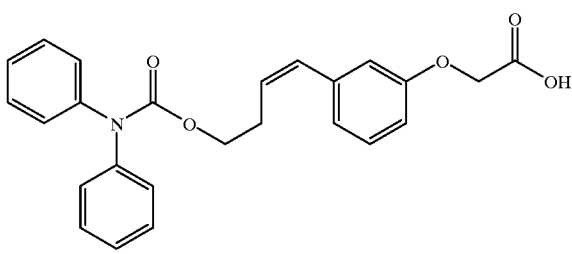

cis-[3-(4-diphenylcarbamoyloxybut-1-enyl)phenoxy]acetic acid;

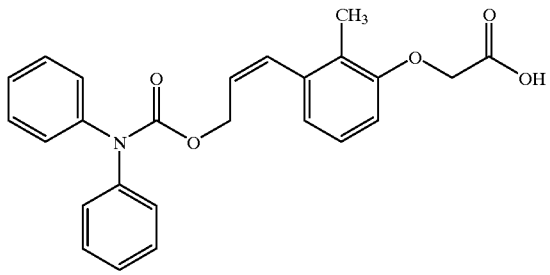

cis-[3-(3-diphenylcarbamoyloxypropenyl)-2-methylphenoxy]acetic acid;

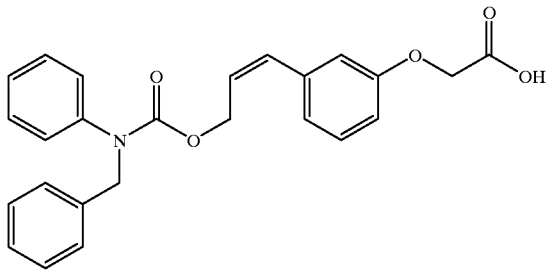

cis-{3-[3-(benzylphenylcarbamoyloxypropenyl)phenoxy] acetic acid;

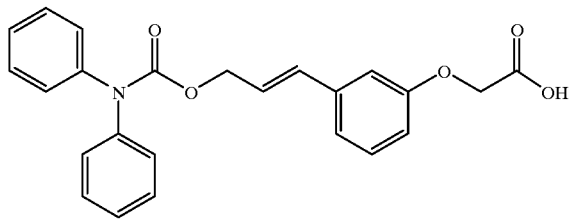

trans-[3-(3-diphenylcarbamoyloxypropenyl)phenoxy}acetic acid; and

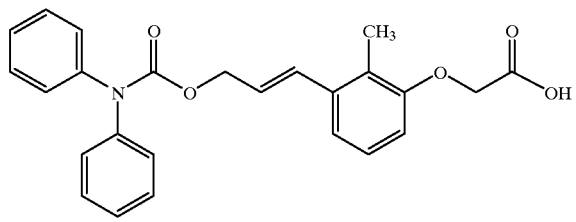

trans-[3-(3-diphenylcarbamoyloxypropenyl)-2-methylphenoxy}acetic acid.

GENERAL SYNTHETIC SCHEME

Compounds of this invention may be made by the methods depicted in the illustrative synthetic reaction schemes shown below.

The starting materials and reagents used in preparing these compounds are either available from commercial suppliers such as Aldrich Chemical Co., or are prepared by methods known to those skilled in the art following procedures set forth in references such as *Fieser and Fieser's Reagents for Organic Synthesis*, Wiley & Sons: New York, 1991, Volumes 1–15; *Rodd's Chemistry of Carbon Compounds*, Elsevier Science Publishers, 1989, Volumes 1–5 and Supplementals; and *Organic Reactions*, Wiley & Sons: New York, 1991, Volumes 1–40. The following schemes are merely illustrative of some methods by which the compounds of this invention can be synthesized, and various modifications to these schemes can be made and will be suggested to one skilled in the art having referred to this disclosure.

The starting materials and the intermediates of the reaction schemes may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C., and most preferably and conveniently at about room (or ambient) temperature, e.g., about 20° C.

Schemes A, B, C, and D describe alternative methods to generate the compounds of Formula I.

Scheme A describes a method of preparing a compound of Formula I wherein B is —O(CH$_2$)$_m$—, and R$^1$, R$^2$, R$^3$, R$^4$, R$^5$, A and m are as defined in the Summary of the Invention.

Scheme A

Scheme A describes a method of preparing a compound of Formula I wherin B is —O(CH$_2$)$_{\overline{m}}$—, and R$^1$, R$^2$, R$^3$, R$^4$, R$^5$, A and m are as defined in the Summary of the Invention.

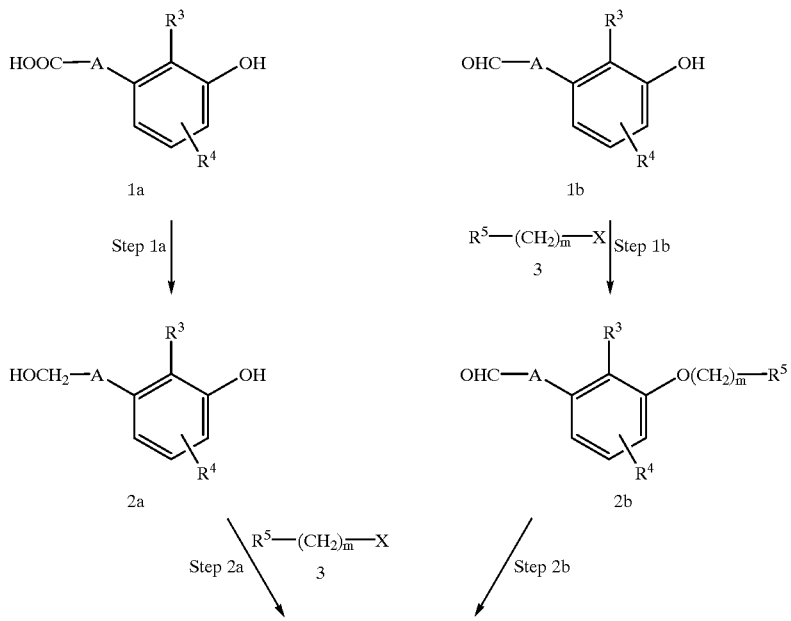

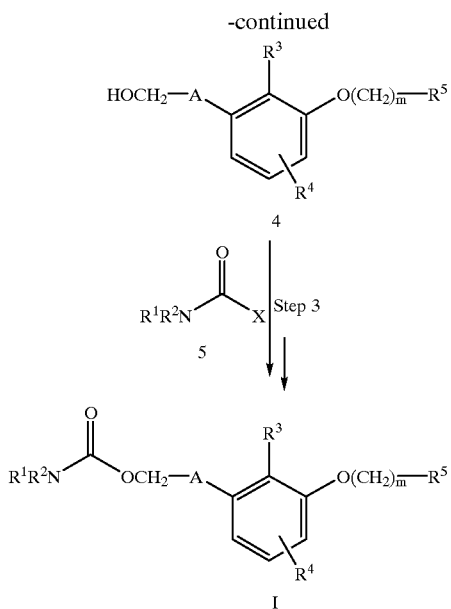

In general, the starting compounds of formula 1a or 1b are commercially available or are known to or can readily be synthesized by those of ordinary skill in the art. For example, synthesis of a compound 1a wherein $R^3$ is bromo and $R^4$ is hydrogen is described by Beijer, P. H., *Rec. Trav. Chim. Pays-Bas.* 1929, 48, 1010, and wherein $R^3$ is chloro and $R^4$ is hydrogen is described by Beuhler et al., *J. Amer. Chem. Soc.* 1946, 68, 574–577.

A compound of formula 1a can also be prepared by the displacement of a 2-methoxy group of 2-(2,3-dimethoxyphenyl)-4,4-dimethyl-4,5-dihydrooxazole with an alkyl group in the presence of a Grignard reagent or an organolithium reagent by methods known to one of ordinary skill in the art. Subsequent hydrolysis of the 4,5-dihydrooxazole group of compound with a strong acid such as aqueous sulfuric acid under modified of Meyers reaction condition, followed by cleavage of the 3-methoxy group to a hydroxy group with a suitable ether cleaving agent such as boron tribromide or concentrated acids such as hydrobromic acid, preferably boron tribromide gives the product compound of formula 1a. Suitable solvents for the reaction include aprotic solvents such as tetrahydrofuran, benzene, toluene, and the like.

In step 1a, a hydroxymethyl phenol 2a is prepared by reducing the carboxylic acid group of compound 1a to an alcohol group by conventional methods. Suitable reducing conditions include lithium aluminum hydride, borane or borane derivatives in an aprotic organic solvent such as diethyl ether, dioxane, tetrahydrofuran, and the like. The compound 2a can also be prepared by cleaving the phthaloyl group of a 3-hydroxyphthalic anhydride and subsequent reduction of the product to a diol. Suitable anhydride cleaving and reducing conditions include lithium aluminum hydride, boranes or borane complexes in an aprotic organic solvent such as tetrahydrofuran, diethyl ether, dioxane, glycol ethers, and the like.

In step 2a, a hydroxymethylphenoxy carboxylic ester 4 can be prepared by alkylating the hydroxy group of compound 2a with a suitable alkylating agent 3 of the formula $R^5$—$(CH_2)_m$—X wherein $R^5$ is a protected carboxyl group and X is halogen, particularly bromo or chloro. The reaction proceeds in the presence of a weak base such as potassium carbonate, cesium carbonate, sodium carbonate, and the like under Williamson synthesis conditions. Suitable inert organic solvents for the reaction include aprotic organic solvents such as acetone, dioxane, tetrahydrofuran, and the like. The alkylating agents 3 are commercially available or can be synthesized by one of ordinary skill in the art.

Alternatively, in step 1b, a formylphenoxy carboxylic ester 2b is prepared by alkylating the hydroxy group of compound 1b with a suitable alkylating agent 3 of the formula $R^5$—$(CH_2)_m$—X as described in step 2a above. Additionally, compound 2b can be synthesized by methods known to one in the art, such as by the oxidation of the primary alcohol group to the corresponding aldehyde group by suitable oxidizing agents such as dimethyl sulfoxide, acetic anhydride, oxalyl chloride, tosyl chloride, and the like. For example, synthesis of a compound of formula 2b wherein $R^3$ is methyl, $R^4$ is hydrogen, $R^5$ is carboxylic acid tert-butyl ester, and m is 1, is described by Marx, M. and Tidwell, T., *J. Org. Chem,* 1984, 49, 788–793.

Alternatively, in step 2b, a hydroxymethylphenoxy carboxylic ester 4 can be prepared by reducing the aldehyde group of compound 2b to an alcohol group by conventional methods. Suitable aldehyde reducing conditions include reduction by lithiated hydrides such as lithium aluminum hydride, or borohydrides such as sodium borohydride, or hydrogenation using a platinum or palladium catalyst in a suitable protic solvent. Additionally, a compound of formula 4 wherein A is a branched alkylene group may be prepared treating compound 2b with an organometallic reagent such as Grignard reagent or an alkyllithium reagent. Suitable solvents for the reaction include aprotic organic solvents such as tetrahydrofuran, diethyl ether, and the like.

In step 3, a compound of Formula I can be prepared by a various methods known to one skilled in the art. For example, the compound of Formula I can be prepared by acylating compound 4 with an acylating agent 5 of the formula $R^1R^2NC(O)X$, wherein X is halogen, particularly bromo or chloro. The reaction proceeds in the presence of a strong base such as lithium alkylamides, alkyllithiums, or potassium bis(trimethylsilyl)amide. Suitable inert organic solvents for the reaction include aprotic organic solvents such as diethyl ether, tetrahydrofuran, and the like. The acylating agents 5 are commercially available, or are known to or can readily be synthesized by those of ordinary skill in the art. For example, synthesis of the compound 5 with varying $R^1$ and $R^2$ can be prepared by treating the corresponding amine of the formula $R^1R^2NH$ with an acyl halide such as oxalyl chloride, phosgene or phosgene equivalents, and the like.

The compound of Formula I wherein $R^5$ is —$COOR^6$ or tetrazolyl, is generally prepared as a protected group and then deprotected by conventional methods to obtain the final product. For example, the compound of Formula I wherein $R^5$ is —$COOR^6$ is prepared as a protected carboxyl group such an alkyl ester, followed by deprotection to obtain the carboxylic acid. The reaction proceeds in the presence of a strong base such as aqueous lithium hydroxide, sodium hydroxide or potassium hydroxide in a protic organic solvent such as methanol, ethanol, water, and mixtures thereof.

The compound of Formula I wherein $R^5$ is tetrazolyl, can be prepared as a protected tetrazolyl such as the triphenylmethyl(trityl)tetrazolyl, followed by deprotection. The compound 2a can be treated with an alkylating agent of the formula N≡C—$(CH_2)_m$—X wherein X is halogen, particularly bromo or chloro. The reaction proceeds in the presence of a weak base such as potassium carbonate, cesium carbonate, or sodium carbonate, in an aprotic organic solvent such as acetone, dioxane, tetrahydrofuran, N,N-dimethylformamide, and the like. In a following step, the cyano product is reacted with an acylating agent 5 of the formula $R^1R^2NC(O)X$, wherein X is halogen, particularly bromo or chloro, and then with a sodium azide which adds to the cyano group with subsequent cyclization to form the tetrazolyl group. The reaction proceeds in the presence of a catalyst such as ammonium chloride, in an aprotic organic solvent such as acetone, dioxane, tetrahydrofuran, N,N-dimethylformamide, and the like. Alternatively, trimethylsilyl or trimethyltin azide can be used to introduce the azide group without catalysis.

Exemplary preparations of a compound of 1a are given in Preparation 1. Exemplary preparations of a compound of Formula I utilizing the reaction conditions described in Scheme A are given in Examples 1 to 5.

Scheme B describes an alternative method of preparing a compound of Formula I, particularly a trans isomer of a compound of Formula I wherein A is alkenylene, B is —$O(CH_2)_m$—, $R^1$, $R^2$, $R^3$, $R^4$, $R^5$, and m are as defined in the Summary of the Invention.

Scheme B

Scheme B describes an alternative method of preparing a compound of Formula I, particularly a trans somer of a compound of Formula I wherein A is alkenylene, B is ——$O(CH_2)_{\overline{m}}$——, $R^1$, $R^2$, $R^3$, $R^4$, $R^5$, and m are as defined in the Summary of the Invention

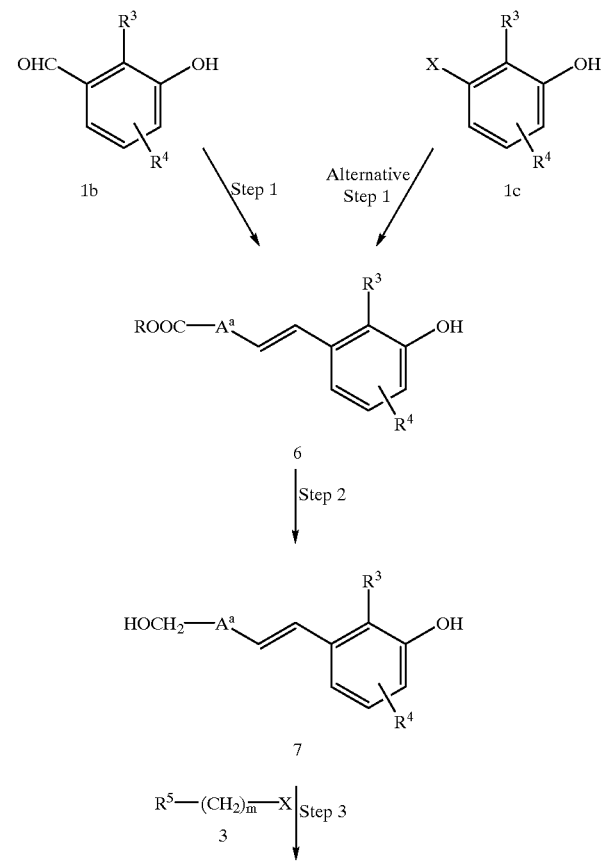

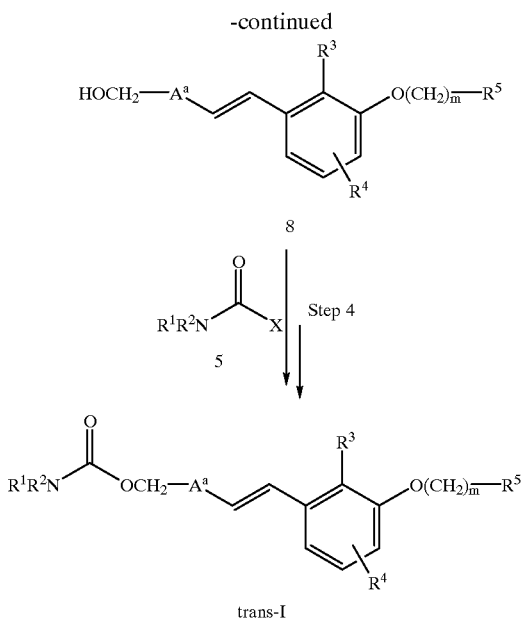

The alternative starting compounds, a hydroxybenzaldehyde 1b or a halogenated phenol 1c wherein X is halogen, preferably bromo or iodo, are commercially available, for example from Aldrich Chemical Company, or are known to or can readily be synthesized by those of ordinary skill in the art.

In step 1, a trans-hydroxyphenylalkylenyl carboxylic ester 6 wherein R is ($C_1$–$C_4$)alkyl and $A^a$ is a bond, alkylene or alkenylene, can be prepared by conditions known to one in the art. For example, compound 6 can be prepared by reacting the aldehyde 1b with an alkylidenetriphenylphosphorane or alkylidene phosphonate that is generated in situ by treatment of a phosphonium salt or a phosphonate such as an alkyl phosphonoacetate with a strong base such lithium hydride or sodium hydride under Wittig or Horner reaction conditions. Compound 6 can also be prepared by treating the aldehyde 1b with 1,8-diazabicyclo[5.5.0]undec-7-ene (DBU) and lithium halide under reaction conditions described by Blanchette, M. A. et al., *Tetrahedron Letters*, 1984, 25, 2183. Suitable solvents for the olefination reaction include inert aprotic solvents such as acetonitrile, tetrahydrofuran, and the like.

In alternative step 1, a trans-hydroxyphenylalkylenyl carboxylic ester 6 wherein R is ($C_1$–$C_4$)alkyl can also be prepared by reacting the halogenated phenol 1c with an acrylic ester such as ethyl acrylate in the presence of phosphine ligand such as tri-(o-tolyl)phosphine in combination with a palladium salt such as palladium(II) acetate. The reaction proceeds in the presence of a base such as triethylamine under an inert atmosphere, for example under Heck-type coupling reaction conditions. Suitable solvents for the reaction include aprotic solvents such as acetonitrile, tetrahydrofuran, and the like.

In step 2, a trans-hydroxyphenylalkylenyl alcohol 7 is prepared by selectively reducing the carboxylic ester group of compound 6 to the corresponding alcohol group. Suitable carboxylic ester reducing conditions include lithium borohydride, lithium aluminum hydride, diisobutylaluminum hydride (DIBAL-H), borane or borane derivatives. The preferred reducing condition is described by Trost, B. M. et al., *J. Org. Chem*, 1980, 45, 1838, and includes the use of a salt called the ate complex formed from DIBAL-H and an alkyllithium compound such as n-butyllithium. Suitable aprotic solvents for the reaction include tetrahydrofuran, hexane, dimethoxyethane, dioxane, and the like.

In step 3, a trans-hydroxymethylalkylenyl phenoxy carboxylic ester 8 is prepared by proceeding as described in Scheme A, step 2a, for example by alkylating the hydroxy group of compound 7 with a suitable alkylating agent 3 of the formula $R^5$—$(CH_2)_m$—X, wherein $R^5$ is a protected carboxyl group.

In step 4, a trans isomer of a compound of Formula I is prepared by proceeding as described in Scheme A, step 3, for example, by acylating compound 8 with an acylating agent 5 of the formula $R^1R^2NC(O)X$, wherein X is halogen, particularly bromo or chloro.

Optionally, a compound of Formula I wherein A is alkylene can be prepared by selectively hydrogenating the carbon-carbon double bond of the product or any of the intermediate compounds synthesized prior to the final product, to obtain the corresponding saturated compounds. Suitable selective reducing conditions include catalytic reduction such as Raney nickel, palladium on carbon, nickel boride, platinum metal or its oxide, and the like, preferably palladium metal or its oxide. Suitable solvents for the reaction include inert organic solvents such as ethyl acetate, methanol, and the like. Preferably, compounds 6, 7, or 8 are selectively hydrogenated to obtain compounds of Formula I wherein A is alkylene.

Exemplary preparations of a trans isomer of a compound of Formula I utilizing the reaction conditions described in Scheme B are given in Examples 6 and 7. Exemplary preparations of a compound of Formula I wherein A is alkylene utilizing the reaction conditions described in Scheme B are given in Examples 11 and 12.

Scheme C describes an alternative method of preparing a compound of Formula I, particularly a cis isomer of a compound of Formula I wherein A is alkenylene, B is —$O(CH2)_m$—, $R^1$, $R^2$, $R^3$, $R^4$, $R^5$, and m are as defined in the Summary of the Invention.

Scheme C

Scheme C describes an alternative method of preparing a compound of Formula I, particularly a cis isomer of a compound of Formula I wherein A is alkenylene, B is —O(CH$_2$)$_{\overline{m}}$—, R$^1$, R$^2$, R$^3$, R$^4$, R$^5$, and m are as defined in the Summary of the Invention.

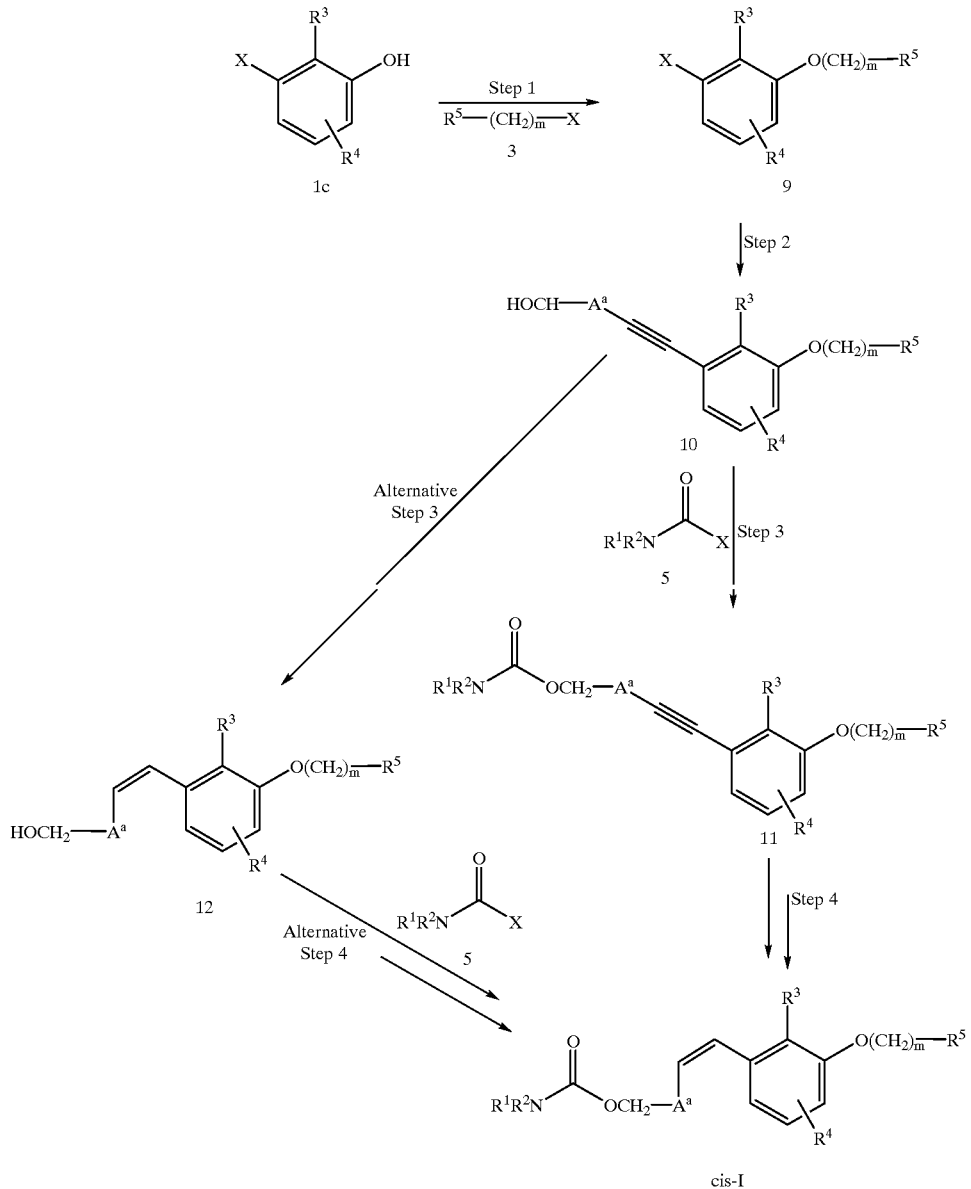

The starting halogenated phenol 1c wherein X is halogen, preferably bromo or iodo, is commercially available, for example from Aldrich Chemical Company, or is known to or can readily be synthesized by those of ordinary skill in the art.

In step 1, a halophenoxy carboxylic ester 9 is prepared by proceeding as described in Scheme A, step 2a, for example by alkylating the hydroxy group of compound 1c with a suitable alkylating agent 3 of the formula R$^5$—(CH$_2$)$_m$—X, wherein R$^5$ is a protected carboxyl group.

In step 2, an hydroxymethylalkynyl phenoxy carboxylic ester 10 wherein A$^a$ is a bond, alkylene or alkenylene, is prepared by reacting compound 9 with an alkynyl alcohol such as propargyl alcohol under acetylene coupling reaction conditions. The reaction proceeds in the presence of a organopalladium catalyst such as tetrakis (triphenylphosphine)palladium(0) or bis (triphenylphosphine)palladium(II) chloride optionally in the presence of a copper halide catalyst such as copper(I) iodide. A suitable solvent for the reaction includes pyrrolidine, which additionally serves as a reagent. Alternatively, the reaction can proceed in the presence of diisopropylamine, optionally in the presence of a copper halide catalyst, in a suitable aprotic solvent such as tetrahydrofuran.

In step 3, a alkynylphenoxy carboxylic ester 11 is prepared by proceeding as described in Scheme A, step 3, for example by acylating compound 10 with an acylating agent 5 of the formula $R^1R^2$ NC(O)X, wherein X is halogen, particularly bromo or chloro.

In step 4, a cis isomer of a compound of Formula I is prepared selectively converting the triple bond of compound 11 to a cis-double bond under partial hydrogenation conditions. Suitable catalysts for the selective partial hydrogenation of alkynes to cis-alkenes include diisobutylaluminum hydride (DIBAL) or hydrogen with a palladium catalyst such as Lindlar Catalyst. The reaction proceeds with the addition of selectivity enhancing agent such as quinoline in a protic organic solvent such as methanol.

In alternative step 3, a cis-hydroxymethylalkenyl phenoxy carboxylic ester 12 is prepared by selectively converting the triple bond of compound 10 to a cis-double bond under partial hydrogenation conditions described in step 3 above.

In alternative step 4, a cis isomer of a compound of Formula I is prepared by proceeding as described in Scheme A, step 4, for example by acylating compound 12 with an acylating agent 5 of the formula $R^1R^2$NC(O)X, wherein X is halogen, particularly bromo or chloro.

Optionally, a compound of Formula I wherein A is alkylene can be prepared by selectively hydrogenating the carbon-carbon double bond of the product or any of the intermediate compounds synthesized prior to the final product, to obtain the corresponding saturated compounds. Suitable selective reducing conditions include catalytic reduction such as Raney nickel, palladium on carbon, nickel boride, platinum metal or its oxide, and the like, preferably palladium metal or its oxide. Suitable solvents for the reaction include inert organic solvents such as ethyl acetate, methanol, and the like. Preferably, compounds 10, 11, or 12 are selectively hydrogenated to obtain compounds of Formula I wherein A is alkylene.

Exemplary preparations of the cis isomer of a compound of Formula I utilizing the reaction conditions described in Scheme C are given in Examples 8 to 10.

Scheme D describes an alternative method of preparing a compound of Formula Ia wherein A is alkenylene, B is —$(CH_2)_n$—, and $R^1$, $R^2$, $R^3$, $R^4$, $R^5$, and n are as defined in the Summary of the Invention.

Scheme D

Scheme D describes an alternative method of preparing a compound of Formula Ia wherein A is alkenylene, B is ——O$(CH_2)_n$——, and $R^1$, $R^2$, $R^3$, $R^4$, $R^5$, and n are as defined in the Summary of the Invention.

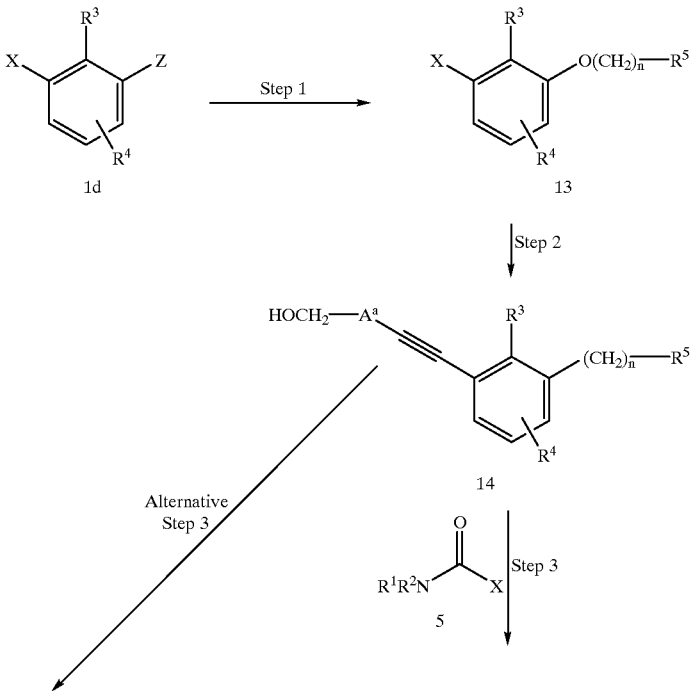

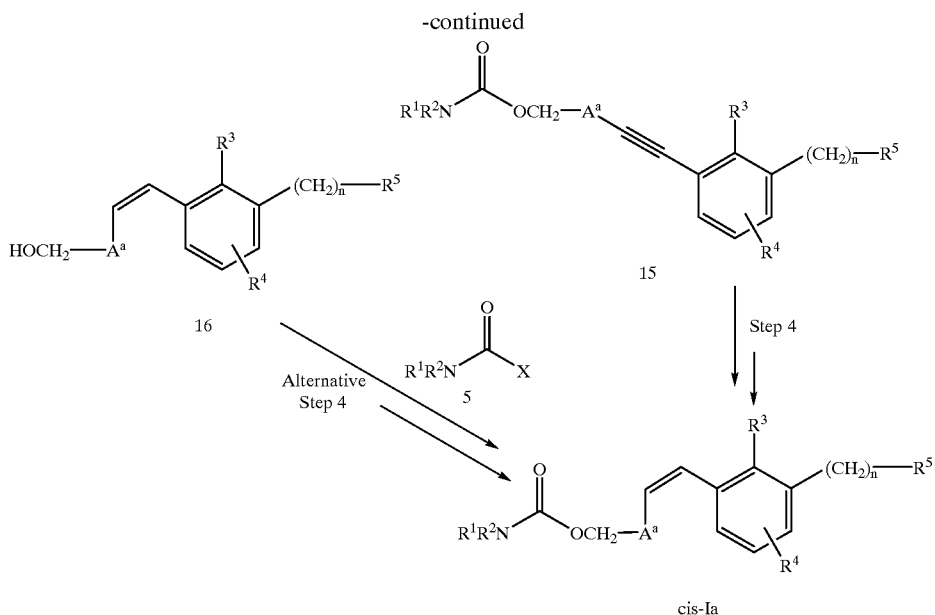

cis-Ia

The cis isomer of a compound of Formula Ia wherein B is —(CH$_2$)$_n$— is synthesized in a manner similar to that described in Scheme C, but utilizing appropriate starting compounds to obtain desired final product.

The starting compound 1d wherein X is halogen, preferably bromo or iodo, and Z is halogen, preferably bromo or iodo, or —CHO or —(CH$_2$)$_n$COOH wherein n is as defined in the Summary of the Invention, is commercially available, for example from Aldrich Chemical Company, or is known to or can readily be synthesized by those of ordinary skill in the art.

In step 1, a halophenyl carboxylic ester 13 wherein A$^a$ is a bond, alkylene or alkenylene, can be prepared by various methods. For example, compound 13 wherein n is 3 is prepared by coupling compound 1d wherein X and Z are each halogen with a vinyl carboxylic ester such as methyl-3-butenoate in the presence of a hydroborating agent such as 9-borabicyclo[3.3.1]nonane dimer (9-BBN). The reaction proceeds in the presence of coupling catalysts such as palladium chloride and tripotassium phosphate in an aprotic solvent such as dichloromethane, N,N-dimethylformamide, tetrahydrofuran, and the like. Transesterification of the resulting carboxylic ester product is effected by treatment with an alcohol such as 2-methyl-2-propanol and a base such as n-butyllithium under an inert atmosphere.

Alternatively, the compound 13 wherein n is 2 can also be prepared by treating compound 1d wherein X is halogen and Z is —CHO with an alkylidene-triphenylphosphorane or alkylidene phosphonate that is generated in situ by the presence of a phosphonium salt or a phosphonate such as an alkyl phosphonoacetate with a strong base such lithium hydride or sodium hydride under Wittig or Horner reaction conditions. The resulting alkenyl carboxylic ester product is selectively hydrogenated to obtain the corresponding saturated compound. Suitable selective reducing conditions include catalytic reduction such as Raney nickel, palladium on carbon, nickel boride, platinum metal or its oxide, and the like, in an inert organic solvent such as ethyl acetate, methanol, and the like.

In step 2, a hydroxymethylalkynylphenyl carboxylic ester 14 is prepared by proceeding as described in Scheme C, step 2, for example by treating compound 13 with an alkynyl alcohol such as propargyl alcohol. Alternatively, compound 14 wherein n is 0 or 1 can be directly prepared by reacting the starting compound 1d wherein X is halogen and Z is —(CH$_2$)$_n$COOH wherein n is 0 or 1, respectively, with an alkynyl alcohol such as propargyl alcohol.

In steps 3 and 4, or in alternative steps 3 and 4, a compound of cis isomer of a compound of Formula Ia is then prepared by proceeding correspondingly as described in Scheme C.

Optionally, a compound of Formula Ia wherein A is alkylene and B is —(CH$_2$)$_n$— can be prepared by selectively hydrogenating the carbon-carbon double bond of the product or any of the intermediate compounds synthesized prior to the final product, to obtain the corresponding saturated compounds. Suitable selective reducing conditions include catalytic reduction such as Raney nickel, palladium on carbon, nickel boride, platinum metal or its oxide, and the like, preferably palladium metal or its oxide. Suitable solvents for the reaction include inert organic solvents such as ethyl acetate, methanol, and the like. Preferably, compounds 14, 15, or 16 are selectively hydrogenated to obtain compounds of Formula Ia wherein A is alkylene.

Exemplary preparations of a compound of Formula Ia utilizing the reaction conditions described in Scheme D are given in Examples 13 to 15.

General Utility

The compounds of the present invention are IP receptor modulators, in particular IP receptor agonists, and as such possess selective agonist activity at the IP receptor. These compounds (and compositions containing them) are expected to be useful in the prevention and treatment of a variety of diseases in mammals, especially humans, related directly or indirectly to blood flow disease states.

In particular, the compounds of this invention are expected to find utility in the treatment of disease states associated with cardiovascular disease states, including, but not limited to, peripheral arterial occlusive diseases (PAOD) such as intermittent claudication, critical limb ischemia, thrombotic diseases, atherosclerosis, thromboangiitis obliterans (Buerger's disease), Raynaud's syndrome, Takayashu's disease, migratory superficial vein thrombophlebitis, acute arterial occlusion, coronary artery disease, restenosis following angioplasty, stroke, and recurrent myocardial infarction.

The compounds of the present invention are also useful in the treatment of hypertensive disease states including, but not limited to, general hypertension, pulmonary hypertension, occular hypertension, and tinnitus associated with hypertension.

Additionally, the compounds of the present invention are useful in treating disease states associated with ischemia including, but not limited to, ischemia associated with allograft transplantation, such as renal transplantation or other organ transplantations. The compounds of the present invention are also of use in the treatment of renal disease states including, but not limited to, renal failure, improper diuresis, improper natriuresis, and improper kaliuresis.

The compounds of the present invention may be use to treat other disease states associated with disease states including, but not limited to, improper wound healing, tissue necrosis, premature uterine contractions, gastric ulcerations, sexual dysfunction in males and females, severe menstrual pain, improper immunoregulation, improper platelet aggregation, and improper neutrophil function.

As a result of the alleviation of the blood flow disease state, the underlying pain causally related to this disease state may also be lessened or eliminated. For example, use of the compounds of the present invention may provide relief of peripheral neuropathies associated with, e.g., diabetic neuropathy, post-traumatic pain, post-surgical pain, pain associated with chemotherapy, etc.

These and other therapeutic uses are described, for example, in *Goodman & Gilman's, The Pharmacological Basis of Therapeutics*, ninth edition, McGraw-Hill, New York, 1996, Chapter 26, 601–616; Coleman, R. A., *Pharmacological Reviews*, 1994, 46:205–229; *Harrison's Principals of Internal Medicine*, fourteenth edition, McGraw-Hill, New York, 1998, 1398–1403; *Handbook of Phase I/II Clinical Drug Trials*, O'Grady, J. and Joubert, P. H. editors, CRC Press, New York, 1997, 249–278.

Testing

The IP receptor agonist affinity of compounds of this invention can be determined using radioligand displacement from human platelet membranes which express an endogenous IP receptor or Chinese Hamster Ovary cells expressing the recombinant rat IP receptor. The latter assay is described in more detail in Example 23.

The IP receptor agonist potency of compounds of this invention can be determined by measuring cyclic AMP accumulation in an assay utilizing either human platelets or Chinese Hamster Ovary cells expressing the recombinant rat IP receptor. The latter assay is described in more detail in Example 24.

The putative efficacy of the IP receptor agonist compounds can be identified in a canine model of peripheral vascular disease. This assay has been established as an animal model for intermittent claudication, and is described in more detail in Example 25.

Administration and Pharmaceutical Composition

The invention includes a pharmaceutical composition comprising a compound of the present invention including isomers, racemic or non-racemic mixtures of isomers, or pharmaceutically acceptable salts or solvates thereof together with one or more pharmaceutically acceptable carriers, and optionally other therapeutic and/or prophylactic ingredients.

In general, the compounds of this invention will be administered in a therapeutically effective amount by any of the accepted modes of administration for agents that serve similar utilities. Suitable dosage ranges are 1–2500 mg daily, preferably 1–1500 mg daily, and most preferably 1–500 mg daily, depending upon numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compounds of this invention for a given disease.

In general, compounds of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is oral using a convenient daily dosage regimen which can be adjusted according to the degree of affliction.

The compounds of the invention, together with a conventional adjuvant, carrier, or diluent, may be placed into the form of pharmaceutical compositions and unit dosages. The pharmaceutical compositions and unit dosage forms may comprise of conventional ingredients in conventional proportions, with or without additional active compounds or principles, and the unit dosage forms may contain any suitable effective amount of the active ingredient commensurate with the intended daily dosage range to be employed. The pharmaceutical composition may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing one thousand (1000) milligrams of active ingredient or, more broadly, one hundred (100) milligrams to five hundred (500) milligrams, per tablet, are accordingly suitable representative unit dosage forms.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is a mixture with the finely divided active component. In tablets, the active component is mixed with the carrier having the necessary binding capacity in suitable proportions and compacted in the shape and size desired. The powders and tablets preferably containing from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in *Remington: The Science and Practice of Pharmacy* 1995, edited by E. W. Martin, Mack Publishing Company, 19th edition, Easton, Pa. Representative pharmaceutical formulations containing a compound of the present invention are described in Examples 16 to 22.

EXAMPLES

The following preparations and examples are given to enable those skilled in the art to more clearly understand and to practice the present invention. They should not be considered as limiting the scope of the invention, but merely as being illustrative and representative thereof.

Preparation 1

Preparation of Compounds of Formula 1a

1A. Preparation of 3-hydroxymethyl-2-methylbenzoic acid

A solution of 3-amino-2-methylbenzoic acid (43.1 g, 285 mmol), water (700 mL), and sulfuric acid (55 mL) was briefly heated to give a clear solution and then cooled to a temperature below 5° C. A solution of sodium nitrite (21 g, 300 mmol) in a minimal amount of water was added in portions while maintaining the internal temperature below 7° C. After stirring for about 30 minutes in an ice bath, urea (7 g) was added to discharge the excess nitrile. A chilled solution of 98% sulfuric acid (240 mL) in water (1000 mL) was added to the diazonium solution, and the combined reaction mixture was heated slowly to 90° C. Solid sodium hydroxide (410 mg) was slowly added. The mixture was extracted with ethyl acetate, and the organic layer was dried over sodium sulfate and evaporated to give 3-hydroxy-2-methylbenzoic acid as a yellow solid (44.4 g,~100%).

1B. Preparation of 3-hydroxy-2-isopropylbenzoic acid 2-(2,3-Dimethoxyphenyl)-4,4-dimethyl-4,5-dihydrooxazole was prepared by utilizing the method described by A. I. Meyers et al., *J. Org. Chem.*, 1978, 43, 1372–1379.

Isopropylmagnesium chloride (2.0M in diethyl ether) (18.75 ml, 37.5 mmol) was added dropwise to a solution of 2-(2,3-dimethoxyphenyl)-4,4-dimethyl-4,5-dihydrooxazole (7.06 g, 30.0 mmol) in freshly distilled tetrahydrofuran at room temperature. The mixture was stirred overnight, quenched with water, and diluted with diethyl ether. The layers were separated, and the aqueous layer was washed twice with diethyl ether. The combined organic extracts were dried over anhydrous sodium sulfate, and concentrated in vacuo. Purification by silica gel flash chromatography, eluting with hexane/ethyl acetate, gave 2-(2-isopropyl-3-methoxyphenyl)-4,4-dimethyl-4,5-dihydrooxazole as a clear oil (7.08 g, 95.4%).

A solution of 2-(2-isopropyl-3-methoxyphenyl)-4,4-dimethyl-4,5-dihydrooxazole (6.18 g, 25 mmol) in 35% solution of sulfuric acid (40 mL) was stirred at reflux for 48 hours. Upon cooling, solid sodium hydroxide (18.15 g) was slowly added. The reaction mixture was extracted with diethyl ether, and the combined organic extracts were extracted with sodium bicarbonate solution. The bicarbonate extracts were then acidified with 3N hydrochloric acid, filtered and dried to give 2-isopropyl-3-methoxybenzoic acid as a white crystalline solid (1.73 g, 35.7%).

A solution of 1M boron tribromide in dichloromethane (15 mL, 15 mmol) was added dropwise to a solution of 2-isopropyl-3-methoxybenzoic acid in dichloromethane. After stirring for 2 hours, the reaction mixture was cooled to 0° C., quenched with water, and the layers were separated. The aqueous layer was extracted with dichloromethane. The combined organic extracts were dried over anhydrous sodium sulfate and concentrated in vacuo. Purification of the residue by silica gel flash chromatography, eluting with dichloromethane/methanol and 1% acetic acid, gave 3-hydroxy-2-isopropylbenzoic acid as a white crystalline solid (1.32 g, 97.5%).

1C. Preparation of 3-hydroxy-2-phenylbenzoic acid

2M Aqueous sodium bicarbonate (10 mL) was added to a suspension of 2-bromo-3-methoxybenzoic acid ethyl ester (2.06 g, 7.7 mmol), benzeneboronic acid (1.11 g), and tetrakis(triphenylphosphine)palladium(0) (0.30 g) in toluene (35 mL) under a nitrogen atmosphere. The mixture was stirred at 80° C. for 2 hours, poured into water, and extracted with diethyl ether. The organic layer was evaporated, and the residue was chromatographed, eluting with hexane/acetone (3:1) to give a semisolid oil. Recrystallization from diethyl ether/hexane gave 3-methoxy-2-phenylbenzoic acid ethyl ester as colorless crystals (0.69 g, 34%).

3-methoxy-2-phenylbenzoic acid ethyl ester (0.53 g) and pyridine hydrochloride (6 g) were combined under nitrogen, then heated to 180° C. for 1 hour. The melt was poured into dilute aqueous hydrochloric acid and extracted with ethyl acetate. Purification by silica gel chromatography, eluting with hexane/acetone (2:1) with 0.5% acetic acid, gave 3-hydroxy-2-phenylbenzoic acid as a white solid (0.25 g, 58%).

Example 1

{2-Chloro-3-[(diphenylcarbamoyloxy)methyl]phenoxy}acetic acid

1A. Preparation of 2-chloro-3-hydroxymethylphenol

2-Chloro-3-hydroxybenzoic acid was synthesized utilizing the method described in Buehler et al., *J. Amer. Chem. Soc.* 1946, 68, 574–577.

A solution of 2-chloro-3-hydroxybenzoic acid (2.59 g, 15 mmol) in tetrahydrofuran was added dropwise to a solution of borane (48 mmol) in tetrahydrofuran (150 mL) at a temperature of 0° C. The reaction mixture was then warmed to 60° C. and allowed to stir overnight. Upon cooling, the mixture was quenched with water and made basic with 3M sodium hydroxide. The aqueous layer was separated, acidified with 3M hydrochloric acid, and extracted with dichloromethane. The combined organic extracts were dried over sodium sulfate and concentrated in vacuo. Recrystallization from ethanol/hexane gave 2-chloro-3-hydroxymethylphenol as a white crystalline solid (1.63 g, 64.8%).

1B. Preparation of (2-chloro-3-hydroxymethylphenoxy)acetic acid methyl ester

Cesium carbonate (3.42 g, 10.5 mmol) was added to a solution of 2-chloro-3-hydroxymethylphenol (1.59 g, 10 mmol) in acetone at room temperature, and the reaction mixture allowed to stir for 30 minutes. Methyl bromoacetate (1.68 g, 11 mmol) was then added. The mixture was stirred overnight, filtered, and the filtrate was concentrated in vacuo. Purification of the residue by silica gel flash chromatography, eluting with dichloromethane/methanol, gave (2-chloro-3-hydroxymethylphenoxy)acetic acid methyl ester as a white crystalline solid (1.94 g, 84.1%).

1C. Preparation of {2-chloro-3-[(diphenylcarbamoyloxy)methyl]phenoxy}acetic acid A solution of (2-chloro-3-hydroxymethylphenoxy)acetic acid methyl ester (1.94 g, 8.41 mmol) in tetrahydrofuran was cooled to −78° C., treated with potassium bis(trimethylsilyl)amide (10.1 mmol), and allowed to stir at −78° C. for about an hour. A solution of diphenylcarbamyl chloride (2.92 g, 12.6 mmol) in tetrahydrofuran was added dropwise, and the resulting mixture was allowed to warm to room temperature and stirred overnight. The mixture was quenched with water, diluted with diethyl ether, and the layers were separated. The aqueous layer was extracted twice more with diethyl ether. The combined organic extracts were dried over sodium sulfate and concentrated in vacuo. Purification of the residue by silica gel flash chromatography, eluting with hexane/acetone (4:1), gave {2-chloro-3-[(diphenyl-carbamoyloxy)methyl]phenoxy}acetic acid methyl ester as a white crystalline solid (1.72g, 48.0%).

{2-Chloro-3-[(diphenylcarbamoyloxy)methyl]phenoxy}acetic acid methyl ester (0.64 g, 1.5 mmol) was dissolved in a mixture of methanol (20 mL), water (5 mL), and tetrahydrofuran (2 mL). An aqueous solution of lithium hydroxide (0.07 g, 1.65 mmol) was added and the mixture was allowed to stir overnight. The mixture was concentrated in vacuo, and the residue diluted with water and washed with diethyl ether. The aqueous layer was acidified with 3M hydrochloric acid forming a white precipitate which was filtered and dried. Recrystallization from methanol gave {2-chloro-3-[(diphenylcarbamoyloxy)methyl]phenoxy}acetic acid as white needles (0.47 g, 76.5%); m.p. 182.2–182.9° C.; $^1$H NMR 4.66 (s, 2H), 5.30 (s, 2H), 6.83 (dt, J=7.5Hz, 2H), 7.11 (t, J=8.0Hz), 7.28 (m, 10H); $^{13}$C NMR 64.98 (t), 66.02 (t), 112.96 (d), 121.62 (d), 126.27 (d), 126.93 (d), 127.02 (d), 128.94 (d), 135.79 (s), 142.34 (s), 153.68 (s), 154.27 (s), 170.26 (s). Analysis for $C_{22}H_{18}ClNO_5$: Calcd.: C, 64.16; H, 4.41; N, 3.40. Found: C, 64.30; H, 4.39; N, 3.56.

Example 2

{3-[(Diphenylcarbamoyloxy)methyl]-2-methylphenoxy}acetic acid

2A. Preparation of 3-hydroxymethyl-2-methylphenol

A solution of 3-hydroxy-2-methylbenzoic acid (44.4 g, 285 mmol) (prepared as described in Preparation 1A) dissolved in dry tetrahydrofuran (200 mL) was added to 1 M borane in tetrahydrofuran (800 mL) while stirring at a temperature of 0° C. The resulting semisolid mixture was heated in a mantle to just short of reflux and heating was maintained for about 15 hours. Methanol (200 mL) was added to the reaction mixture. The resultant clear solution was evaporated in vacuo and then evaporated with further portions of methanol to give 3-hydroxymethyl-2-methylphenol (30.3 g, 99%).

2B. Preparation of (3-hydroxymethyl-2-methylphenoxy)acetic acid tert-butyl ester Tert-butyl bromoacetate (75 g, 385 mmol) was added to a solution/suspension of 3-hydroxymethyl-2-methylphenol (46.6 g, 337 mmol) and finely powdered potassium carbonate (60 g) in acetone (500 mL). The mixture was heated at reflux for about 40 hours or until the reaction was complete. The solids were filtered, and the liquid residue was evaporated. Purification of the residue by silica gel chromatography, eluting with acetone/hexane, gave (3-hydroxymethyl-2-methylphenoxy)acetic acid tert-butyl ester as a pale yellow oil (80.1 g, 96%).

2C. Preparation of {3-[(diphenylcarbamoyloxy)methyl]-2-methylphenoxy}acetic acid A solution of (3-hydroxymethyl-2-methylphenoxy)acetic acid te/t-butyl ester (80.1 g, 318 mmol) dissolved in tetrahydrofuran (400 mL) was cooled to −50° C. and treated with lithium diisopropylamide (325 mmol) freshly prepared from diisopropylamine (49 mL) and 2.5M n-butyllithium (130 mL) in tetrahydrofuran (100 mL). After about 10 minutes at −50° C., a solution of diphenylcarbamyl chloride (80.8 g, 350 mmol) dissolved in tetrahydrofuran (100 mL) was added. The entire reaction mixture was stirred for an additional 30 minutes and then allowed to warm to room temperature over a period of 3 hours. The solution was evaporated in vacuo, poured into dilute hydrochloric acid, and extracted with diethyl ether. The organic layer was dried over brine, evaporated, and purified by silica gel chromatography, eluting with acetone/hexane (1:5→1:3), to give {3-[(diphenylcarbamoyloxy)-methyl]-2-methylphenoxy}acetic acid tert-butyl ester as a white solid (104.1 g, 73%).

{3-[(Diphenylcarbamoyloxy)methyl]-2-methylphenoxy}acetic acid tert-butyl ester (104.1 g, 233 mmol) and lithium hydroxide (10.3 g, 245 mmol) were dissolved in a mixture of water (100 mL), methanol (300 mL), and tetrahydrofuran (300 mL). The mixture became solid, but reliquefied upon heating at reflux temperature. The clear solution was stirred at room temperature for about 16 hours, and evaporated in vacuo. The residue was poured into dilute hydrochloric acid and extracted with dichloromethane. Evaporation of the solvent and recrystallization of the residue from hexane/acetone gave {3-[(diphenylcarbamoyloxy)methyl]-2-methylphenoxy}acetic acid as off-white granules (87.0 g, 95%); m.p. 180.1–180.7° C. Analysis for $C_{23}H_{21}NO_5$: Calcd.: C, 70.58; H, 5.41; N, 3.58. Found: C, 70.51; H, 5.37; N, 3.76.

Example 3

3A. Proceeding as described in Example 2, but substituting 3-hydroxy-2-methylbenzoic acid in Example 2A with other compounds of formula 1a and proceeding correspondingly, the following compounds of Formula I were prepared:

{2,6-dimethyl 3-[(diphenylcarbamoyloxy)methyl]phenoxy}acetic acid; m.p. 177.6–178.1° C. $^1$HNMR 2.21 (s, 3H), 2.27 (s, 3H), 4.62 (s, 2H), 5.30 (s, 2H), 6.65 (d, J=8.4 Hz, 1H), 6.93 (d, J=8.4Hz, 1H), 7.22 (m, 10H). $^{13}$C NMR 11.83(q), 19.25(q), 62.53(t), 65.67(t), 112.19(d), 126.14(d), 126.90(d), 128.02(d), 128.07(d), 128.88(d), 131.96(s), 134.02(s), 142.51(s), 153.88(s), 154.79(s), 172.66(s).

Analysis for $C_{24}H_{23}NO_5+0.1H_2O$: Calcd: C, 70.78; H, 5.74; N, 3.44. Found C, 70.52; H, 5.67; N, 3.52.

{2-bromo-3-[(diphenylcarbamoyloxy)methyl]phenoxy}acetic acid; m.p. 188.2–189.0° C. Analysis for $C_{20}H_{18}BrNO_5$: Calcd.: C, 57.91; H, 3.98; N, 3.07. Found: C, 57.91; H, 3.98; N, 3.13.

{3-[(diphenylcarbamoyloxy)methyl]-2-phenylphenoxy}acetic acid; m.p. 181.0–181.5° C. Analysis for $C_{28}H_{23}NO_5$: Calcd.: C, 74.16; H, 5.11; N, 3.09. Found: C, 73.84; H, 5.15; N, 3.19.

{3-[(diphenylcarbamoyloxy)methyl]-2-ethylphenoxy)acetic acid; m.p. 160.9–161.7° C. $^1$H NMR 0.95 (t, J=7.4 Hz, 3H), 2.57 (q, J=7.4, 2H), 4.69 (s, 2H), 5.17 (s, 2H), 6.79 (d, J=7.9 Hz, 1H), 6.81 (d, J=7.9 Hz, 1H), 7.08 (t, J=7.9, 1H), 7.30 (m, 10H), 12.98 (bs, 1H). $^{13}$C NMR 13.79(q), 18.58(t), 64.60(t), 64.92(t), 111.27(d), 121.35(d), 126.28(d), 127.07 (d), 128.91(d), 130.80(s), 134.65(s), 142.26(s), 153.74(s), 155.45(s), 170.19(s). Analysis for $C_{24}H_{23}NO_5$: Calcd.: C, 71.10; H, 5.72; N, 3.45. Found: C, 70.98; H, 5.71; N, 3.61.

{3-[(diphenylcarbamoyloxy)methyl]-2-propylphenoxy}acetic acid; m.p. 51.0–54.0° C. $^1$H NMR: 0.858(t, J=7.4 Hz, 3H), 1.41 (sextet, J=7.4 Hz, 2H), 2.56(t, J=7.7 Hz, 2H), 4.33(s, 2H), 5.17(s, 2H), 6.76(t, J=8.8 Hz, 2H), 7.02(t, J=8.0 Hz, 1H), 7.29(m, 10H). $^{13}$C NMR: 14.44(q), 22.33(t), 27.58(t), 65.18(t), 66.50(t), 111.49(d), 120.71(d), 126.12(d), 126.31 (d), 127.12(d), 128.97(d), 129.29(s), 134.64(s), 142.34(s), 153.84(s), 156.43(s), 170.43(s). Analysis for $C_{25}H_{25}NO_5.0.55H_2O$: Calcd.: C, 69.83; H, 6.12; N, 3.39. Found: C, 69.93; H, 6.13; N, 3.26.

{3-[(diphenylcarbamoyloxy)methyl]-2-isopropylphenoxy}acetic acid tert-butylamine salt (0.49 g, 58.4%); m.p. 173.7–182.2° C. $^1$H NMR δ (ppm) 1.19 (s, 3H), 1.21 (s, 9H), 3.05 (septet, J=6.8 Hz, 1H), 4.16 (s, 2H), 5.12 (s, 2H), 6.7 (d, J=7.6 Hz, 1H), 6.74 (d, J=8.4 Hz, 1H), 6.98 (tr, J=7.9 Hz, 1H), 7.29 (m, 10H), 8.33 (br s, 3H); $^{13}$C NMR δ (ppm) 20.50 (q), 27.41 (q), 28.06 (d), 50.13(s), 66.32 (t), 67.89 (t), 113.09 (d), 121.59 (d), 126.02 (d), 126.24 (d), 127.23 (d), 129.00 (d), 133.49 (s), 134.37 (s), 142.39 (s), 153.84 (s), 158.15 (s), 171.13 (s). Analysis for $C_{25}H_{25}NO_5.C_4H_{11}N$: Calcd.: C, 70.71; H, 7.37; N, 5.69. Found: C, 70.75; H, 7.39; N, 5.84.

3B. A solution of 3-hydroxyphthalic anhydride (0.77 g, 4.7 mmol) dissolved in tetrahydrofuran (15 mL) was refluxed with borane-tetrahydrofuran complex (20 mL) for 18 hours. The resulting suspension was cooled and decomposed with excess methanol (gas evolution), and the solvents were removed under vacuum. The residue was evaporated with methanol to give (2,3-bis-hydroxymethyl)phenol as a white solid (0.72 g, 98%). Subsequently proceeding as described in Example 2, but substituting 3-hydroxymethyl-2-methylphenol in Example 2B with (2,3-bis-hydroxymethyl) phenol and proceedingly correspondingly in Example 2C, the following compound of Formula I was prepared:

{3-[(diphenyl-carbamoyloxy)methyl]-2-hydroxymethylphenoxy}acetic acid; m.p. 137.2–137.9° C. Analysis for $C_{23}H_{21}NO_6$: Calcd.: C, 67.81; H, 5.20; N, 3.44. Found: C, 67.81; H, 5.24; N, 3.57.

3C. Proceeding as described in Example 2, but substituting diphenylcarbamyl chloride in Example 2C with N-phenyl-N-pyridin-3-ylcarbamyl chloride or N-cyclohexyl-N-phenylcarbamyl chloride and proceedingly correspondingly, the following compounds of Formula I were prepared:

{2-methyl-3-[(phenylpyridin-3-ylcarbamoyloxy)methyl] phenoxy}acetic acid; m.p. 180.1–180.7° C. Analysis for $C_{22}H_{20}N_2O_5 \cdot 0.35H_2O$: Calcd.: C, 66.27; H, 5.23; N, 7.03. Found: C, 66.41; H, 5.36; N, 6.76.

{3-[(cyclohexylphenylcarbamoyloxy)methyl] phenoxy}acetic acid; m.p. 175.5–176.2 0 C.; $^1H$ NMR 0.90 (m, 1H), 1.10 (m, 2H), 1.32 (m, 2H), 1.53 (m, 1H), 1.71 (m, 2H), 1.89 (m, 2H), 2.10 (s, 3H), 4.15 (m, 1H), 4.58 (s, 2H), 5.08 (s, 2H), 6.70 (m, 2H), 7.06 (m, 3H), 7.32 (m, 3H); $^{13}C$ NMR 11.04(q), 25.28(t), 25.83(t), 31.96(t), 56.85(d), 65.37 (t), 65.73(t), 111.23(d), 121.60(d), 125.90(s), 125.98(d), 127.45(d), 128.61(d), 130.05(d), 136.45(s), 138.20(s), 156.20(s), 171.21(s).

Analysis for $C_{23}H_{27}NO_5$: Calcd.: C, 69.50; H, 6.85; N, 3.52. Found: C, 69.36; H, 6.85; N, 3.7.

Example 4

{3-[(Diphenylcarbamoyloxy)methyl]phenoxy}acetic acid

4A. Preparation of (3-formylphenoxy)acetic acid methyl ester

Powdered potassium carbonate (5 g) was added to a solution of 3-hydroxybenzaldehyde (3.1 g, 25 mmol) and methyl bromoacetate (4.6 g, 30 mmol) dissolved in acetone (40 mL), and the mixture was stirred under reflux for 4 hours. The reaction mixture was then poured into excess water, extracted with dichloromethane, and evaporated. The resultant yellow oil was distilled on the Kugelrohr (1 mmHg, 150° C.) to give (3-formylphenoxy)acetic acid methyl ester as a colorless oil (4.53 g, 93%).

4B. Preparation of (3-hydroxymethylphenoxy)acetic acid methyl ester A solution of sodium borohydride (1 g) dissolved in water (10 mL) was rapidly added to a solution of (3-formylphenoxy)acetic acid methyl ester (4.53 g) dissolved in methanol (50 mL). After about 10 minutes, the resultant clear solution was acidified with excess 10% aqueous hydrochloric acid, poured into water, extracted with dichloromethane, and the solvents evaporated. Chromatography over silica gel, eluting with 5% acetone/dichloromethane, gave (3-hydroxymethylphenoxy)acetic acid methyl ester as a colorless oil (2.51 g, 55%).

4C. Preparation of {3-[(diphenylcarbamoyloxy)methyl] phenoxy}acetic acid (3-Hydroxymethylphenoxy)acetic acid methyl ester (400 mg, 2 mmol) and diphenylcarbamyl chloride (580 mg, 2.5 mmol) were combined in pyridine (2 ml). The resultant yellow solution was allowed to stand for ten days under nitrogen. The mixture was then poured into water, extracted with dichloromethane, and evaporated. Purification of the residue by silica gel chromatography, eluting with 5% acetone/dichloromethane, gave {3-[(diphenyl-carbamoyloxy)methyl]phenoxy}acetic acid methyl ester as a colorless solid (575 mg, 73%).

{3-[(Diphenyl-carbamoyloxy)methyl]phenoxy}acetic acid methyl ester was hydrolyzed by proceeding as described in Example 2C to give {3-[(diphenylcarbamoyloxy)methyl]phenoxy}acetic acid as a white solid (353 mg, 65%); m.p. 142.2–143.8° C.; $^1$HNMR 4.63 (s, 2H), 5.11 (s, 2H), 6.82 (m, 3H), 7.30 (m, 11H), 12.80 (bs, 1H). Analysis for $C_{22}H_{19}NO_5$: Calcd: C, 70.02; H, 5.07; N, 3.71. Found: C, 70.06; H, 5.07; N, 3.89.

Example 5

{3-[(1-Diphenylcarbamoyloxy)ethyl]-2-methylphenoxy}acetic acid

5A. Preparation of (3-formyl-2-methylphenoxy)acetic acid tert-butyl ester (3-Hydroxymethyl-2-methylphenoxy)acetic acid tert-butyl ester was prepared by utilizing the method described by Marx, M. and Tidwell, T., *J. Org. Chem,* 1984, 49, 788–793.

Oxalyl chloride (0.46 mL, 5.25 mmol) was added dropwise to a solution of dimethyl sulfoxide (0.88 mL, 12.50 mmol) dissolved in dichloromethane (40 mL). The mixture was cooled to −78° C. and allowed to stir for 1 hour. A solution of (3-hydroxymethyl-2-methylphenoxy)acetic acid tert-butyl ester (1.26, 5.00 mmol) in dichloromethane was cannulated into the reaction mixture and allowed to stir at −78° C. for an additional hour. Triethylamine (3.49 mL, 25 mmol) was added. The reaction mixture was allowed to warm to room temperature, poured into water, and the layers were separated. The aqueous layer was extracted twice with dichloromethane. The combined organic extracts were washed with 2N hydrochloric acid and saturated sodium bicarbonate, dried over anhydrous sodium sulfate, and concentrated in vacuo. Purification by silica gel chromatography, eluting with hexane/acetone, gave (3-formyl-2-methylphenoxy)acetic acid tert-butyl ester as a slightly yellow crystalline solid (1.07 g, 85.9%).

5B. Preparation of [3-(1-hydroxyethyl)-2-methylphenoxy] acetic acid tert-butyl ester (3-Formyl-2-methylphenoxy)acetic acid tert-butyl ester (0.94 g, 3.75 mmol) was dissolved in freshly distilled tetrahydrofuran and cooled to −78° C. Methyl magnesium chloride (2.62 mL, 7.88 mmol) was added dropwise and the mixture was allowed to stir at −78° C. for two hours. The mixture was allowed to warm to room temperature, stirred for an additional six hours, then carefully quenched with water, and extracted with ethyl acetate. The organic extracts were dried over anhydrous sodium sulfate and concentrated in vacuo. Purification by silica gel chromatography, eluting with hexane/acetone, gave [3-(1-hydroxyethyl)-2-methylphenoxy)acetic acid tert-butyl ester as a clear oil (594 mg, 59.5%).

5C. Preparation of [3-(1-diphenylcarbamoyloxy)ethyl)-2-methylphenoxy]acetic acid

[3-(1-Hydroxyethyl)-2-methylphenoxy)acetic acid tert-butyl ester (553 mg, 2.00 mmol) and diphenylcarbamyl chloride (695 mg, 3.00 mmol) were dissolved in freshly distilled tetrahydrofuran (30 mL) and cooled to cooled to −78° C. Lithium diisopropyl amide (1.20 mL, 2.40 mmol) was added dropwise. The mixture was allowed to warm to room temperature and stirred overnight, quenched with diethyl ether, and the layers were separated. The organic layer was dried over anhydrous sodium sulfate and concentrated in vacuo. Purification by silica gel chromatography, eluting with hexane/acetone (9:1), gave [3-(1- diphenylcarbamoyloxy)ethyl)- 2-methylphenoxy]acetic acid tert-butyl ester as a clear oil (411 mg, 44.5%).

[3-(1-Diphenylcarbamoyloxy)-ethyl)-2-methylphenoxy] acetic acid tert-butyl ester (346 mg, 0.75 mmol) was dissolved in methanol (25 mL) and water (10 mL). An aqueous solution of lithium hydroxide (69 mg, 1.65 mmol) was added and the mixture was stirred at room temperature for 6 hours. The mixture concentrated in vacuo, and the residue was diluted with water and washed with diethyl ether. The aqueous layer was acidified with dilute hydrochloric acid and extracted with dichloromethane. The organic extract was dried over anhydrous sodium sulfate and concentrated in vacuo to give [3-(1-diphenylcarbamoyloxy)ethyl)-2-methylphenoxy]acetic acid as a clear foam (293 mg, 96.4%); mp. 57.0–69.0° C.; $^1$H NMR 1.35 (d, J=6.5 Hz, 3H), 2.13 (s, 3H), 4.67 (s, 2H), 5.96 (q, J=6.5 Hz, 1H), 6.67 (d, J=7.8 Hz, 1H), 6.74 (d, j=8.2 Hz, 1H), 7.08 (t, J=8.0 Hz, 1H), 7.26 (m, 6H), 7.39 (m, 4H), 12.99 (br s, 1H); $^{13}$C NMR 9.56 (q), 20.44 (q), 63.82 (t), 69.83 (d), 109.33 (d), 116.41 (d), 121.56 (s), 125.20 (d), 125.28 (d), 125.99 (d), 127.87 (d), 140.33 (s), 141.21 (s), 154.46 (s), 169.16 (s). Analysis for $C_{22}H_{18}ClNO_5 \cdot 0.14CH_2Cl_2$: Calcd.: C, 69.47; H, 5.62; N, 3.36. Found: C, 69.41; H, 5.62; N, 3.78.

Example 6

Trans-[3-(3-Diphenylcarbamoyloxypropenyl) phenoxy}acetic acid

6A. Preparation of trans-3-(3-hydroxyphenyl)acrylic acid methyl ester

A solution of trimethyl phosphonoacetate (9.94 mL, 61.4 mmol), lithium chloride (2.60 g, 12.2 mmol) and 1,8-diazabicyclo[5.4.0]undec-7-ene (DBU) (15.92 mL, 106.5 mmol) in acetonitrile (80 mL) at room temperature under a nitrogen atmosphere was stirred at room temperature for 30 minutes. 3-Hydroxybenzaldehyde (5.00 g, 40.9 mmol) was added, and the mixture was stirred at room temperature for an additional 3 hours. Water was added and the aqueous phase was extracted with diethyl ether. The combined organic fractions were washed with water, brine, dried over magnesium sulfate, and evaporated to dryness. Purification by flash chromatography, eluting with hexane/ethyl acetate, gave trans- 3-(3-hydroxyphenyl)acrylic acid methyl ester as a white crystalline solid (6.30 g, 86%).

6B. Preparation of trans-3-(3-hydroxypropenyl)phenol

Lithium n-butyldiisobutylaluminum hydride was prepared in situ by adding 1.0M diisobutylaluminum hydride (DIBAL-H) in toluene (16.8 mL, 16.8 mmol) to a solution of 2.5M n-butyllithium in hexane (6.73 mL, 16.8 mmol) at −5° C. under an argon atmosphere. Tetrahydrofuran (70 mL) was added and the mixture was cooled to −78° C. A solution of trans-3-(3-hydroxyphenyl)acrylic acid methyl ester (1.0 g, 5.61 mmol) in tetrahydrofuran (70 mL) was added to the dropwise to the mixture over 15 minutes, and the combined solution was allowed to reach −20° C. and was stirred for 3 hours. The mixture was cooled to −78° C. and sodium sulfate decahydrate (6 g) was added, followed by saturated ammonium chloride (150 mL) and concentrated hydrochloric acid to pH 2–3. The mixture was extracted with dichloromethane, and the extract was washed with water, brine, dried sodium sulfate, and concentrated to dryness. Purification by flash chromatography, eluting with hexane/ethyl acetate, gave pure trans-3-(3-hydroxypropenyl)phenol as a clear crystalline solid (0.58 g, 68%).

6C. Preparation of trans-[3-(3-hydroxypropenyl)phenoxy] acetic acid tert-butyl ester A solution of tert-butyl bromoacetate (0.60 mL, 4.03 mmol) and potassium carbonate (1.12 g, 8.06 mmol) was added to a solution of trans-3-(3-hydroxypropenyl)phenol (0.58 g, 3.84 mmol) in acetone (15 mL) at room temperature under a nitrogen atmosphere and stirred for about 20 hours. The mixture was filtered, and the filtrate was concentrated to dryness. Purification by flash chromatography, eluting with hexane/ethyl acetate, gave pure trans-[3-(3-hydroxypropenyl)phenoxy]acetic acid tert-butyl ester as a clear oil (0.987 g, 97%).

6D. Preparation of trans-[3-(3-diphenylcarbamoyloxypropenyl)phenoxy]acetic acid

A solution of trans-[3-(3-hydroxypropenyl)phenoxy] acetic acid tert-butyl ester (0.50 g, 1.89 mmol) in tetrahydrofuran (15 mL) was added to a solution of 2.0M lithium diisopropylamide in heptane/tetrahydrofuran/ethylbenzene (1.04 mL, 2.08 mmol), and diphenylcarbamyl chloride (0.46 g, 1.98 mmol) at −78° C. under an argon atmosphere. The mixture was allowed to reach 0–5° C. and was maintained at this temperature for 16 hours. Saturated ammonium chloride was added and the product was extracted with dichloromethane. The extract was washed with water, brine, dried over sodium sulfate, and concentrated to dryness. Purification by flash chromatography, eluting with hexane/ethyl acetate (7:3), gave pure trans-[3-(3-diphenylcarbamoyloxypropenyl)phenoxy}acetic acid tert-butyl ester as a white crystalline solid (0.56 g, 65%).

1.0M Lithium hydroxide (1.46 mL, 1.46 mmol) was added to a solution of trans-[3-(3-diphenylcarbamoyloxypropenyl)phenoxy}acetic acid tert-butyl ester (0.56 g, 1.22 mmol) in methanol (2 mL), tetrahydrofuran (2 mL) at room temperature under a nitrogen atmosphere. The mixture was stirred at room temperature for 3 hours. The solvent was evaporated, water was added followed by 2N hydrochloric acid to pH 1–2, and the product was extracted with ethyl acetate. The extract was washed with water, brine, dried over magnesium sulfate, and concentrated to dryness. Recrystallization in diethyl ether gave trans-[3-(3-diphenylcarbamoyloxypropenyl) phenoxy}acetic acid as a white crystalline solid (0.38 g, 78%), m.p. 112.4–113.7° C.

Example 7

Trans-[3-(3-Diphenylcarbamoyloxypropenyl)-2-methylphenoxy}acetic acid

7A. Preparation of trans-3-(3-hydroxy-2-methylphenyl) acrylic acid ethyl ester

Ethyl acrylate (1.16 mL, 10.7 mmol), palladium acetate (60.1 mg, 0.27 mmol), tri-o-tolylphosphine (160 mg, 0.54 mmol) and triethylamine (1.62 mL) were added to a solution of 3-bromo-2-methyl phenol (1 g, 5.35 mmol) in acetonitrile (2.5 mL) under a nitrogen atmosphere. The mixture was heated at 82° C. for 16 hours and cooled. 1N Hydrochloric acid was added, and the mixture was extracted with ethyl acetate. The extract was washed with water and brine, dried under sodium sulfate, and concentrated to dryness. Purification by flash chromatography, eluting with hexane/ethyl acetate, gave trans-3-(3-hydroxy-2-methylphenyl)acrylic acid ethyl ester as a clear oil (480 mg, 43.5%).

7B. Preparation of trans-[3-(3-diphenylcarbamoyloxypropenyl)-2-methylphenoxy]acetic acid Proceeding as described in Example 6, but substituting trans-3-(3-hydroxyphenyl)acrylic acid methyl ester in Example 6B with trans-3-(3-hydroxy-2-methylphenyl) acrylic acid methyl ester, and proceeding correspondingly in Example 6C, trans-[3-(3-diphenylcarbamoyloxypropenyl)-2-methylphenoxy}acetic acid was prepared as a white solid (141 mg, 89%), m.p. 118.0–118.6° C.

Example 8

Cis-[3-(3-Diphenylcarbamoyloxypropenyl)-2-methylphenoxy]acetic acid

8A. Preparation of (3-bromo-2-methylphenoxy)acetic acid tert-butyl ester

Tert-butyl bromoacetate (1.08 mL, 7.27 mmol) and potassium carbonate (2.01 g, 14.55 mmol) were added to a solution of 3-bromo-2-methylphenol (1.29 g, 6.92 mmol) in acetone (17 mL), and the mixture was stirred at room temperature for 5 hours under a nitrogen atmosphere. The mixture was filtered, and the filtrate was evaporated to dryness to give (3-bromo-2-methylphenoxy)acetic acid tert-butyl ester as a pale yellow oil (2.12 g, 100%).

8B. Preparation of [3-(3-hydroxyprop-1-ynyl)-2-methylphenoxy]acetic acid tert-butyl ester Tetrakis(triphenylphosphine)palladium(0) (0.41 g, 0.35 mmol) and propargyl alcohol (0.83 mL, 14.3 mmol) were added to a solution of (3-bromo-2-methylphenoxy)acetic acid tert-butyl ester (2.13 g, 7.08 mmol) in pyrrolidine (21 mL) under an argon atmosphere at room temperature. The mixture was heated at 75–80° C. for 2.5 hours. Excess saturated ammonium chloride was added and the mixture was extracted with diethyl ether. The extract was washed with brine, dried over sodium sulfate, and concentrated to dryness. Purification by flash chromatography, eluting with hexane/ethyl acetate, gave [3-(3-hydroxyprop-1-ynyl)-2-methylphenoxy]acetic acid tert-butyl ester as an oil (0.38 g, 19.5%).

8C. Preparation of [3-(3-diphenylcarbamoyloxyprop-1-ynyl)-2-methylphenoxy]acetic acid tert-butyl ester 2.0 M Lithium diisopropylamide in toluene/heptane/ethylbenzene (0.77 mL, 1.54 mmol) was added to a stirred solution of [3-(3-hydroxyprop-1-ynyl)-2-methylphenoxy]acetic acid tert-butyl ester (370 mg, 1.34 mmol) in tetrahydrofuran (4 mL) at −78° C. under an argon atmosphere. The mixture was stirred for 10 minutes and solid diphenylcarbamyl chloride (310 mg, 1.34 mmol) was added. The mixture was allowed to reach 0–5° C. and stirred for 16 hours. Saturated ammonium chloride was added and the mixture was extracted with ethyl acetate. The extract was washed with brine, dried over sodium sulfate, and concentrated to dryness. Purification by flash chromatography, eluting with hexane/ethyl acetate, gave [3-(3-diphenylcarbamoyloxyprop-1-ynyl)-2-methylphenoxy]acetic acid tert-butyl ester as a colorless oil (220 mg, 35%).

8D. Preparation of cis-[3-(3-diphenylcarbamoyloxypropenyl)-2-methylphenoxy]acetic acid Quinoline (22 μL) and a Lindlar catalyst (22 mg) were added to a solution of [3-(3-diphenylcarbamoyloxyprop-1-ynyl)-2-methylphenoxy]acetic acid tert-butyl ester (215 mg, 0.46 mmol) in methanol (2 mL) under a nitrogen atmosphere. The mixture was stirred for 35 minutes in a balloon filled with hydrogen. The mixture was filtered, and the filtrate was taken to dryness. Purification by flash chromatography, eluting with hexane/ethyl acetate (92.5:7.5), gave cis-[3-(3-diphenylcarbamoyloxypropenyl)-2-methylphenoxy]acetic acid tert-butyl ester as a colorless oil (150 mg, 69.4%).

Lithium hydroxide monohydrate (13 mg, 0.31 mmol) was added to a stirred solution of cis-[3-(3-diphenylcarbamoyloxypropenyl-2-methylphenoxy]acetic acid tert-butyl ester (144 mg, 0.30 mmol) in tetrahydrofuran (1.4 mL), methanol (0.31 mL) and water (0.3 mL) at room temperature under nitrogen. The mixture was stirred for 4 hours at room temperature, 1 N hydrochloric acid was added to pH 1–2, followed by water, and extracted with ethyl acetate. The extract washed with brine, dried over sodium sulfate, and concentrated to dryness. Crystallization from dichloromethane/hexanes gave cis-[3-(3-diphenylcarbamoyloxypropenyl)-2-methylphenoxy]acetic acid as a white solid (141 mg, 89%), m.p. 133.4–135.5° C.

Example 9

Cis-[3-(3-Diphenylcarbamoyloxypropenyl)phenoxy]acetic acid

9A. Preparation of (3-bromophenoxy)acetic acid tert-butyl ester

Tert-butyl bromoacetate (1.88 mL, 12.69 mmol) and potassium carbonate (3.5 g, 25.38 mmol) were added to a solution of 3-bromophenol (2.09 g, 12.08 mmol) in acetone (30 mL), and the mixture was stirred at room temperature for 5 hours under a nitrogen atmosphere. The mixture was filtered, and the filtrate was evaporated to dryness to give (3-bromophenoxy)acetic acid tert-butyl ester as a colorless oil (3.53 g, 100%).

9B. Preparation of [3-(3-hydroxyprop-1-ynyl)phenoxy]acetic acid tert-butyl ester Tetrakis(triphenylphosphine)palladium(0) (0.66 g, 0.57 mmol) and propargyl alcohol (1.34 mL, 22.97 mmol) were added to a solution of (3-bromophenoxy) acetic acid tert-butyl ester (3.3 g, 11.49 mmol) in pyrrolidine (35 mL) under an argon atmosphere at room temperature. The mixture was heated at 75–80° C. for 2.5 hours. Excess saturated ammonium chloride was added and the mixture was extracted with diethyl ether. The extract was washed with brine, dried over sodium sulfate, and concentrated to dryness. Purification by flash chromatography, eluting with hexane/ethyl acetate, gave [3-(3-hydroxyprop-1-ynyl)phenoxy]acetic acid tert-butyl ester as a pale yellow oil (1.93 g, 64%).

9C. Preparation of cis-[3-(3-hydroxypropenyl)phenoxy]acetic acid tert-butyl ester Quinoline (54 μL) and a Lindlar catalyst (54 mg) were added to a stirred solution of [3-(3-hydroxyprop-1-ynyl)phenoxy]acetic acid tert-butyl ester (547 mg, 2.09 mmol) in methanol (4.3 mL) under a nitrogen atmosphere. The mixture was stirred for 1 hour in a balloon filled with hydrogen, filtered, and the filtrate was taken to dryness. The residue was purified by flash chromatography, eluting with hexane/ethyl acetate, dissolved in diethyl ether, and washed with 2 N hydrochloric acid (10 mL) and 10% sodium bicarbonate, dried over sodium sulfate, and concentrated to give cis-[3-(3-hydroxypropenyl)phenoxy]acetic acid tert-butyl ester as a colorless oil (420 mg, 76%).

9D. Preparation of cis-[3-(3-diphenylcarbamoyloxypropenyl)phenoxy]acetic acid 2.0 M Lithium diisopropylamide in a solution of tetrahydrofuran/heptane/ethylbenzene (0.9 mL, 1.8 mmol) was added to a stirred solution of cis-[3-(3-hydroxypropenyl)phenoxy]acetic acid tert-butyl ester (421 mg, 1.56 mmol) in tetrahydrofuran (4.5 mL) at −78° C. under an argon atmosphere. The mixture was stirred for 10 minutes and solid diphenylcarbamoyl chloride (361 mg, 1.56 mmol) was added. The mixture was allowed to reach 0–5° C. and stirred for 16 hours. Saturated ammonium chloride was added, and the mixture was extracted with ethyl acetate. The extract was dried over sodium sulfate, and concentrated to dryness. Purification by flash chromatography, eluting with hexane/ethyl acetate (9:1), gave cis-[3-(3-diphenylcarbamoyloxypropenyl)phenoxy] acetic acid tert-butyl ester (433 mg, 60.4%).

Lithium hydroxide monohydrate (48.2 mg, 1.15 mmol) was added to a stirred solution of cis-[3-(3-hydroxypropenyl)phenoxy]acetic acid tert-butyl ester (421 mg, 1.04 mmol) in tetrahydrofuran (4.9 mL), methanol (1.3 mL) and water (1.2 mL) at room temperature under nitrogen and was stirred for 4 hours at room temperature. 1 N hydrochloric acid was added to pH 1–2, followed by water. The mixture was extracted with ethyl acetate, and the extract washed with brine, dried over sodium sulfate, and concentrated to dryness. The resulting oil was dissolved in diethyl ether (3.5 mL) and tert-butylamine (94 µL) was added. The resulting suspension was filtered and the solid washed with diethyl ether to obtain the tert-butylamine salt of cis-[3-(3-diphenylcarbamoyloxypropenyl)phenoxy]acetic acid (360 mg, 82.5%), m.p. 132.5–135° C.

Example 10

10A. Proceeding as described in either Example 8 or Example 9, but optionally replacing 3-bromo-2-methylphenol in Example 8A or 3-bromophenol in Example 9A with other compounds of formula 1c, or replacing tert-butyl bromoacetate with other compounds of formula 3, or replacing propargyl alcohol with other alkynyl alcohols, and proceedingly correspondingly, the following compounds of Formula I were prepared:

cis-[3-(4-diphenylcarbamoyloxybut-1-enyl)phenoxy] acetic acid tert-butylamine salt; m.p. 112.5–112.8° C., cis-[3-(5-diphenylcarbamoyloxypent-1-enyl)phenoxy] acetic acid tert-butylamine salt; Analysis for $C_{26}H_{25}NO_5$: Calcd.: C, 71.41; H, 7.19; N, 5.55. Found: C, 71.02; H, 7.12; N, 5.54, cis-[3-(6-diphenylcarbamoyloxyhex-1-enyl)phenoxy] acetic acid tert-butylamine salt; m.p. 87.0–88.5° C., cis-4-[3-(3-diphenylcarbamoyloxypropenyl)phenoxy] butyric acid tert-butylamine salt; m.p. 102–106° C., and cis-5-[3-(3-diphenylcarbamoyloxypropenyl)phenoxy] pentanoic acid, m.p. 56.3–56.7° C.

10B. Proceeding as described in either Example 8 or Example 9, but optionally replacing 3-bromo-2-methylphenol in Example 8A or 3-bromophenol in Example 9A with other compounds of formula 1c, and replacing diphenylcarbamyl chloride with other compounds of formula 5, and proceedingly correspondingly, the following compounds of Formula I were prepared:

cis-{3-[3-(methylphenylcarbamoyloxypropenyl) phenoxy]acetic acid tert-butylamine salt; m.p. 152.3–154.2° C.; and cis-{3-[3-(benzylphenylcarbamoyloxypropenyl) phenoxy]acetic acid tert-butylamine salt; m.p. 107.0–108.5° C.

Example 11

[3-(3-Diphenylcarbamoyloxypropyl)phenyl]acetic acid

11A. Preparation of 3-(3-hydroxyphenyl)propionic acid methyl ester

10% Palladium on carbon (0.31 g) was added to a solution of trans-3-(3-hydroxyphenyl)acrylic acid methyl ester (31.0 g, 17.4 mmol) (prepared as described in Example 6A) in ethyl acetate (30 mL) at room temperature under a nitrogen atmosphere. The mixture was hydrogenated under a balloon pressure for 4 hours. The catalyst was filtered, and the filtrate was concentrated to dryness. Crude 3-(3-hydroxyphenyl) propionic acid methyl ester (3.16 g) was directly used in the next step.

11B. Preparation of 3-(3-hydroxypropyl)phenol 1.0M Lithium aluminum hydride in tetrahydrofuran (35.07 mL, 35.07 mmol) was added to a solution of 3-(3-hydroxyphenyl)propionic acid methyl ester (3.16 g, 17.5 mmol) in tetrahydrofuran (30 mL) at 0–5° C. under an argon atmosphere. The mixture was stirred at room temperature for 6 hours, and sodium sulfate decahydrate (15 g) was added to the mixture, followed by cooling to 0–5° C., and a dropwise addition of water (about 10 mL) and concentrated hydrochloric acid to pH 2–3. The mixture was extracted with ethyl acetate, and the extract was washed with water, brine, dried over magnesium sulfate, and concentrated to dryness. Purification by flash chromatography, eluting with hexane/ethyl acetate, gave 3-(3-hydroxypropyl)phenol as a clear oil (2.34 g, 88%).

11C. Preparation of [3-(3-hydroxypropyl)phenoxy]acetic acid tert-butyl ester

Tert-butyl bromoacetate (2.39 mL, 16.2 mmol) and potassium carbonate (4.47 g, 32.3 mmol) were added to a solution of 3-(3-hydroxypropyl)phenol (2.34 g, 15.4 mmol) in acetone. The mixture was stirred at room temperature for about 20 hours, filtered, and the extract concentrated to dryness. Purification by flash chromatography, eluting with hexane/ethyl acetate, gave 3-(3-hydroxypropyl)-phenoxy] acetic acid tert-butyl ester as a clear oil (3.65 g, 89%).

11 D. Preparation of [3-(3-diphenylcarbamoyloxypropyl) phenyl]acetic acid

A solution of 2.0M Lithium diisopropylamide (7.57 mL, 15.1 mmol) and a solution of diphenylcarbamyl chloride (3.35 g, 14.5 mmol) dissolved in tetrahydrofuran (100 mL) was added to a solution of 3-(3-hydroxypropyl)-phenoxy] acetic acid tert-butyl ester in tetrahydrofuran (40 mL). The mixture was allowed to reach 0–5° C. and maintained at this temperature for 16 hours. Saturated ammonium chloride was added and the mixture was extracted with dichloromethane. The organic layer was dried over brine, dried over sodium sulfate, and concentrated to dryness. Purification by silica gel chromatography, eluting with acetone/hexane (7:3), gave [3-(3-diphenylcarbamoyloxy-propyl)phenyl]acetic acid tert-butyl ester as a yellow oil (3.88 g, 61 %). Subsequent hydrolysis of the ester and recrystallization gave [3-(3-diphenylcarbamoyloxypropyl)phenyl]acetic acid as a white crystalline solid (0.47 g, 54%), m.p. 133.7–134.6° C.

Example 12

Proceeding as described in Example 11, but replacing trans-3-(3-hydroxyphenyl)acrylic acid methyl ester in Example 11A with other compounds of formula 6, and proceeding correspondingly the following compounds of Formula I were prepared:

[3-(2-diphenylcarbamoyloxyethyl)phenyl]acetic acid, m.p. 123.0–123.3° C.;

[3-(4-diphenylcarbamoyloxybutyl)phenyl]acetic acid, m.p. 117.8–119.6° C.;

[3-(5-diphenylcarbamoyloxypentyl)phenyl]acetic acid, m.p. 128.1–128.7° C.;

[3-(6-diphenylcarbamoyloxyhexyl)phenyl]acetic acid, m.p. 99.8–101.7° C.;

[3-(3-diphenylcarbamoyloxypropyl)-2-methylphenyl] acetic acid, m.p. 128.7–129.2° C.; and

[3-(3-diphenylcarbamoyloxypropyl)-2-methylphenyl] pentanoic acid, m.p. 81.5–81.9° C;

Example 13 cis-3-[3-(3-Diphenylcarbamoyloxypropenyl)phenyl] propionic acid

13A. Preparation of 3-(3-bromophenyl)acrylic acid tert-butyl ester

A solution of tert-butyldiethyl phosphonoacetate (2.86 mL, 12.2 mmol), lithium chloride (0.52 g, 12.2 mmol) and 1,8-diazabicyclo[5.4.0]undec-7-ene (DBU) (1.57 mL, 10.54 mmol) in acetonitrile (25 mL) at room temperature under a nitrogen atmosphere was stirred at room temperature for 30 minutes. 3-Bromobenzaldehyde (0.95 mL, 10.5 mmol) was added, and the mixture was stirred at room temperature for an additional 3 hours. Water was added and the aqueous phase was extracted with diethyl ether. The combined organic fractions were washed with water, brine, dried over magnesium sulfate, and evaporated to dryness. Purification by flash chromatography, eluting with hexane/ethyl acetate, gave 3-(3-bromophenyl)acrylic acid tert-butyl ester as a clear oil (2.24 g, 97%).

13B. Preparation of 3-(3-bromophenyl)propionic acid tert-butyl ester

Platinum(IV) oxide (0.002 g, 0.032 mmol) was added to a solution of 3-(3-bromophenyl)acrylic acid tert-butyl ester (2.24 g, 7.90 mmol) in methanol (7 mL) and tetrahydrofuran (1 mL) at room temperature under a nitrogen atmosphere. The mixture was hydrogenated under a balloon pressure for 10 hours. The mixture was filtered and the filtrate was concentrated to dryness. Purification by flash chromatography, eluting with hexane/ethyl acetate, gave 3-(3-bromophenyl)propionic acid tert-butyl ester as a clear oil (1.32 g, 58%).

13C. Preparation of 3-[3-(3-hydroxyprop-1-ynyl)phenyl] propionic acid tert-butyl ester Tetrakis(triphenylphosphine)palladium(0) (0.41 g, 0.14 mmol), cuprous iodide (0.5 g, 0.25 mmol), and propargyl alcohol (0.29 mL, 4.91 mmol) were added to a solution of 3-(3-bromophenyl)propionic acid tert-butyl ester (2.13 g, 7.08 mmol) in pyrrolidine (8 mL) under an argon atmosphere at room temperature. The mixture was heated at 75–80° C. for 5 hours. After cooling to room temperature, saturated ammonium chloride was added and the mixture was extracted with diethyl ether. The extract was washed with brine, dried over magnesium sulfate, and concentrated to dryness. Purification by flash chromatography, eluting with hexane/ethyl acetate (85:15), gave 3-[3-(3-hydroxyprop-1-ynyl)phenyl]propionic acid tert-butyl ester as a yellow oil (0.21 g, 33%).

13D. Preparation of cis-3-[3-(3-diphenylcarbamoyloxypropenyl)phenyl]propionic acid Proceeding as described in Example 8, but replacing [3-(3-hydroxyprop-1-ynyl)-2-methylphenoxy]acetic acid tert-butyl ester in Example 8C with 3-[3-(3-hydroxyprop-1-ynyl)phenyl] propionic acid tert-butyl ester, and proceeding correspondingly in Example 8D, gave cis-3-[3-(3-diphenylcarbamoyloxypropenyl)phenyl]propionic acid as a clear oil (0.14 g, 75%) Crystallization from diethyl ether with tert-butylamine gave cis-3-[3-(3-diphenylcarbamoyloxypropenyl)phenyl]propionic acid tert-butylamine salt (570 mg, 75%), m.p. 131.8–132.4° C.

Example 14

14A. Proceeding as described in Example 13, but replacing 3-bromobenzaldehyde with 3-bromophenylacetic acid, replacing propargyl alcohol with another alkynyl alcohol, and proceeding correspondingly, the following compound of Formula Ia was prepared:

cis-[3-(4-diphenylcarbamoyloxybut-1-enyl)phenyl]acetic acid tert-butylamine salt; m.p. 151.2–153.1° C.

14B. Proceeding as described in Example 13, but replacing 1,3-dibromobenzene with 3-iodobenzoic acid in Example 13A, optionally replacing propargyl alcohol with other alkynyl alcohols, and proceeding correspondingly, the following compounds of Formula Ia were prepared:

cis-[3-(3-diphenylcarbamoyloxypropenyl)phenyl] benzoic acid, m.p. 137.5–137.8° C.;

cis-3-(4-diphenylcarbamoyloxybut-1-enyl)benzoic acid tert-butylamine salt, m.p. 172.8–176.8° C.; and cis-3-(3-diphenylcarbamoyloxypropenyl)benzoic acid tert-butylamine salt; m.p. 180.5–184.0° C.

14C. Proceeding as described in Example 13, but replacing 3-bromobenzaldehyde with 3-bromophenylacetic acid, replacing propargyl alcohol with another alkynyl alcohol, hydrogenating the carbon-carbon double to the corresponding saturated bond, and proceeding correspondingly, the following compound of Formula Ia was prepared:

[3-(3-diphenylcarbamoyloxybutyl)phenyl]acetic acid tert-butylamine salt; m.p. 112.3–113.1° C.

Example 15 cis-4-[3-(3-Diphenylcarbamoyloxypropenyl)phenyl] butyric acid

15A. Preparation of 4-(3-bromophenyl)butyric acid methyl ester

[9-Borabicyclo[3.3.1]nonane dimer] (13.4 mL, 6.68 mmol) (9-BBN dimer) was added to a solution of methyl-3-butenoate (0.71 mL, 6.68 mmol) in tetrahydrofuran (2.7 mL) at 0–5° C. under an argon atmosphere, and the mixture was stirred for 4 hours. N,N-Dimethylformamide (27 mL), palladium(II) chloride, dichloromethane (130 g, 0.16 mmol), 1,3-dibromobenzene (0.77 mL, 61.37 mmol) and potassium phosphate (powdered, 1.5 g, 6.94 mmol) were added. The mixture was treated at 50° C. overnight. Water was added and the mixture extracted with diethyl ether. The extract was washed with water, brine, and dried over sodium sulfate, and concentrated to dryness. Purification by flash chromatography, eluting with hexane/ethyl acetate) gave 4-(3-bromophenyl)butyric acid methyl ester as a clear oil (0.26 mg, 16%).

15B. Preparation of 4-(3-bromophenyl)butyric acid tert-butyl ester

N-Butyllithium (4.43 mL, 11.07 mmol) was added to a solution 2-methyl-2-propanol (1.0 mL, 10.53 mmol) in tetrahydrofuran (21 mL) at −10° C. under an argon atmosphere, and the mixture was stirred for 10 minutes. A solution of 4-(3-bromophenyl)butyric acid methyl ester (1.35 g, 5.27 mmol) in tetrahydrofuran (5.3 mL) was added dropwise at −10° C., and the mixture allowed to reach room temperature and stirred for 16 hours. Saturated ammonium chloride was added and the product extracted with ethyl acetate. The extract was dried over sodium sulfate and concentrated to dryness. Purification by flash chromatography, eluting with hexane/ethyl acetate (98:2), gave 4-(3-bromophenyl)butyric acid tert-butyl ester as a yellow oil (74%).

15C. Preparation of cis-4[3-(3-diphenylcarbamoyloxypropenyl)phenyl]butyric acid

Proceeding as described in Example 8, but replacing [3-(3-hydroxyprop-1-ynyl)-2-methylphenoxy]acetic acid tert-butyl ester in Example 8C with 4-(3-bromophenyl) butyric acid tert-butyl ester, and proceeding correspondingly, gave cis-4[3-(3-diphenylcarbamoyloxypropenyl)phenyl]butyric acid as a clear oil (0.14 g, 75%) Crystallization from diethyl ether with tert-butylamine gave cis-4-[3-(3-diphenyl-carbamoyloxypropenyl)phenyl]butyric acid tert-butylamine salt m.p. 112.4–115.3° C.

Example 16

Composition for Oral Administration

| Ingredient | % wt./wt. |
| --- | --- |
| Active ingredient | 20.0% |
| Lactose | 79.5% |
| Magnesium stearate | 0.5% |

The ingredients are mixed and dispensed into capsules containing 100 mg each; one capsule would approximate a total daily dosage.

Example 17

Composition for Oral Administration

| Ingredient | % wt./wt. |
| --- | --- |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Example 18

Composition for Oral Administration

| Ingredient | % wt./wt. |
| --- | --- |
| Active ingredient | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

Example 19

Parenteral Formulation (IV)

| Ingredient | % wt./wt. |
| --- | --- |
| Active ingredient | 0.25 g |
| Sodium Chloride | Qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

Example 20

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 21

Topical Formulation

| Ingredients | Grams |
| --- | --- |
| Active compound | 0.2–2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

Example 22

Nasal Spray Formulations

Several aqueous suspensions containing from 0.025–0.5 percent active compound are prepared as nasal spray formulations. The formulations optionally contain inactive ingredients such as microcrystalline cellulose, sodium carboxymethylcellulose, dextrose, and the like. Hydrochloric acid may be added to adjust pH. The nasal spray formulations may be delivered via a nasal spray metered pump typically delivering 50–100 microliters of formulation per actuation. A typical dosing schedule is 2–4 sprays every 4–12 hours.

Example 23

IP Receptor Binding Assay

The IP receptor affinity of compounds of this invention was determined using a radioligand displacement assay utilizing Chinese Hamster Ovary cells expressing the rat recombinant IP receptor. This assay is a modification of well-established procedures using [$^3$H] iloprost as the radioligand.

Chinese Hamster Ovary cells expressing the rat recombinant IP receptor were maintained in Hams F-12 media with 10% fetal bovine serum and 250 µg/ml geneticin, under 5% carbon dioxide at 37° C. The cells were harvested over ice using 2 mM EDTA in phosphate buffered saline (calcium/magnesium free, 4° C.) and centrifuged at 500×g. Cell number was determined and the pellet stored at −70° C.

The pellets were thawed at room temperature and then diluted in the assay buffer (20 mM Tris-HCL, 5 mM magnesium chloride, pH 7.4) to the appropriate concentration and briefly homogenized. The pellet suspension was lastly added to assay tubes containing the buffer, test compound, and radioligand. The assay tubes were incubated at 25° C. for 1 hour, rinsed three times with ice cold assay buffer, and the bound radioactivity determined using liquid scintillation counting.

For each test compound, the concentration producing 50% inhibition of binding ($IC_{50}$) and Hill slope was determined using iterative curve fitting techniques. The inhibition dissociation constant (Ki) of each test compound was determined according to the method of Cheng and Prusoff (1973).

A number of compounds of the invention were evaluated and found to be active in this assay with a pKi range from about 4.8 to about 7.2.

Example 24

IP Receptor Agonist Activity Assay

The IP receptor agonist potency of compounds of this invention was determined by measuring the agonist-mediated cyclic AMP accumulation in an assay utilizing Chinese Hamster Ovary cells expressing the rat recombinant IP receptor. Cyclic AMP levels were determined using a commercially available Adenylate Cyclase cAMP Flash-plate Assay (New England Nuclear).

Chinese Hamster Ovary cells expressing the rat recombinant IP receptor were maintained in Ham's Mixture with 10% fetal bovine serum and 250 µg/ml geneticin under 5% carbon dioxide (95% $O_2$) at 37° C. Cells were harvested at approximately 90% confluency using Dulbecco's Phosphate-Buffered saline containing 2 mM EDTA, and washed once at 1000×g and resuspended in Wash Buffer. A sample was aliquoted for protein determination. The cell suspension was centrifuged at 1000×g and adjusted to 110–140 E+3 cells/50 µl in the "Stimulation and Detection Buffer" from the assay kit.

The test compounds or vehicle were incubated with 50 µl cells (110–140 E+3 cells) for 5 minutes at room temperature. After the incubation, 100 µl lysis/tracer solution was added to the wells and the radioactivity counted on a Packard Topcount microplate scintillation counter after overnight incubation. The amount of radioactive cAMP bound to the antibody is inversely proportional to the concentration of added non-radioactive cAMP. The $pEC_{50}$ values were then determined and compared against standard agonist values.

A number of compounds of the invention were evaluated and found to be active in this assay with a $pEC_{50}$>4.82 for stimulation of intracellular cAMP.

Example 25

Canine Model for Intermittent Claudication

The putative efficacy of the IP receptor agonist compounds can be identified in a canine model of peripheral vascular disease. The alleviation of symptoms of intermittent claudication may be determined by measuring the exercise capacity in dogs with surgically induced acute hind limb arterial insufficiency using a modification of the method described in Bohm, E. et al., *Arch.Pharmacol.* 1990, 341, Suppl. R61.

Briefly, prior to surgery involving femoral ligation/ablation and occlusion of small arterioles with superfine Sephadex, the dogs were trained to exercise on a treadmill and the exercise capacity (rate and speed) for each dog was measured based on time to clinical symptoms (limping or failure to continue treadmill exercise). Five to ten days after the surgical preparation, exercise tolerance was again measured until it reached presurgical baseline exercise capacity.

The end point of exercise testing was the observation of claudication clinical signs such as limping, or failure to continue treadmill exercise. Blood flow to the normal and surgically manipulated hind limb was measured 1–3 times per week prior and/or after treadmill exercise.

The response of post-surgery day is compared to the pre-surgery day using a paired t test. The difference between the treatment group and the control group is tested using a two-sample t test at each testing day.

In this model, the compounds of this invention increased the running time on a treadmill compared to control animals during a specified time interval following surgical intervention. Dogs trained on a treadmill exhibited a dramatic decrease in running time following femoral artery ablation surgery. Typically dogs require 21–28 days following surgery to regain normal running time on the treadmill; however, dogs treated with compounds of the invention regained normal running times within 5–10 days after treatment.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A compound comprising Formula I:

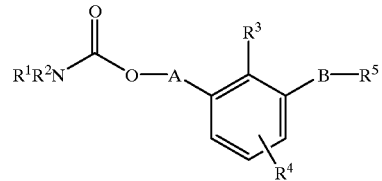

I wherein:
$R^1$ and $R^2$ are each independently in each occurrence alkyl, aryl, aralkyl, heteroaryl, cycloalkyl, or heterocyclyl;

$R^3$ and $R^4$ are each independently in each occurrence hydrogen, alkyl, alkoxy, amino, halogen, haloalkyl, hydroxyalkyl, nitro, aryl, aralkyl, or heterocyclyl;

$R^5$ is independently in each occurrence —$COOR^6$ or tetrazolyl;

$R^6$ is independently in each occurrence hydrogen or alkyl;

A is independently in each occurrence alkylene or alkenylene;

B is independently in each occurrence —$O(CH_2)_m$— or —$(CH_2)_n$—;

m is independently in each occurrence an integer from 1 to 8 inclusive;

n is independently in each occurrence an integer from 0 to 8 inclusive;

or an individual isomer, a racemic or non-racemic mixture of isomers, or a pharmaceutically acceptable salt or solvate thereof.

2. The compound of claim 1 wherein $R^1$ and $R^2$ are each independently aryl or aralkyl.

3. The compound of claim 2 wherein $R^1$ and $R^2$ are each independently phenyl or benzyl.

4. The compound of claim 3 wherein $R^3$ and $R^4$ are each independently hydrogen, alkyl, aryl, aralkyl, or halogen.

5. The compound of claim 4 wherein $R^3$ and $R^4$ are each independently hydrogen, methyl, ethyl, n-propyl, isopropyl, butyl, phenyl, benzyl, bromo, or chloro.

6. The compound of claim 5 wherein $R^5$ is —$COOR^6$.

7. The compound of claim 6 wherein $R^6$ is hydrogen.

8. The compound of claim 7 wherein A is alkylene, B is —$O(CH_2)_m$—, and m is an integer from 1 to 5 inclusive.

9. The compound of claim 7 wherein A is alkylene, B is —$(CH_2)_n$—, and n is an integer from 0 to 5 inclusive.

10. The compound of claim 7 wherein A is alkenylene, B is —$O(CH_2)_m$—, and m is an integer from 1 to 5 inclusive.

11. The compound of claim 7 wherein A is alkenylene, B is —$(CH_2)_n$—, and n is an integer from 0 to 5 inclusive.

12. The compound of claim 1 which is:
[3-[diphenylcarbamoyloxy)methyl]-2-methylphenoxy}acetic acid,
[3-(3-diphenylcarbamoyloxypropyl)phenyl]acetic acid,
cis-{3-[3-(benzylphenylcarbamoyloxypropenyl)phenoxy]acetic acid,
cis-[3-(3-diphenylcarbamoyloxypropenyl)phenoxy]acetic acid,
cis-[3-(4-diphenylcarbamoyloxybut-1-enyl)phenoxy]acetic acid,
cis-[3-(3-diphenylcarbamoyloxypropenyl)-2-methylphenoxy]acetic acid,
cis-3[3-(3-diphenylcarbamoyloxypropenyl)phenyl]propionic acid,
trans-[3-(3-diphenylcarbamoyloxypropenyl)phenoxy}acetic acid, or
trans-[3-(3-diphenylcarbamoyloxypropenyl)-2-methylphenoxy}acetic acid;
or an individual isomer, a racemic or non-racemic mixture of isomers, or a pharmaceutically acceptable salt or solvate thereof.

13. The compound of claim 1 which is:

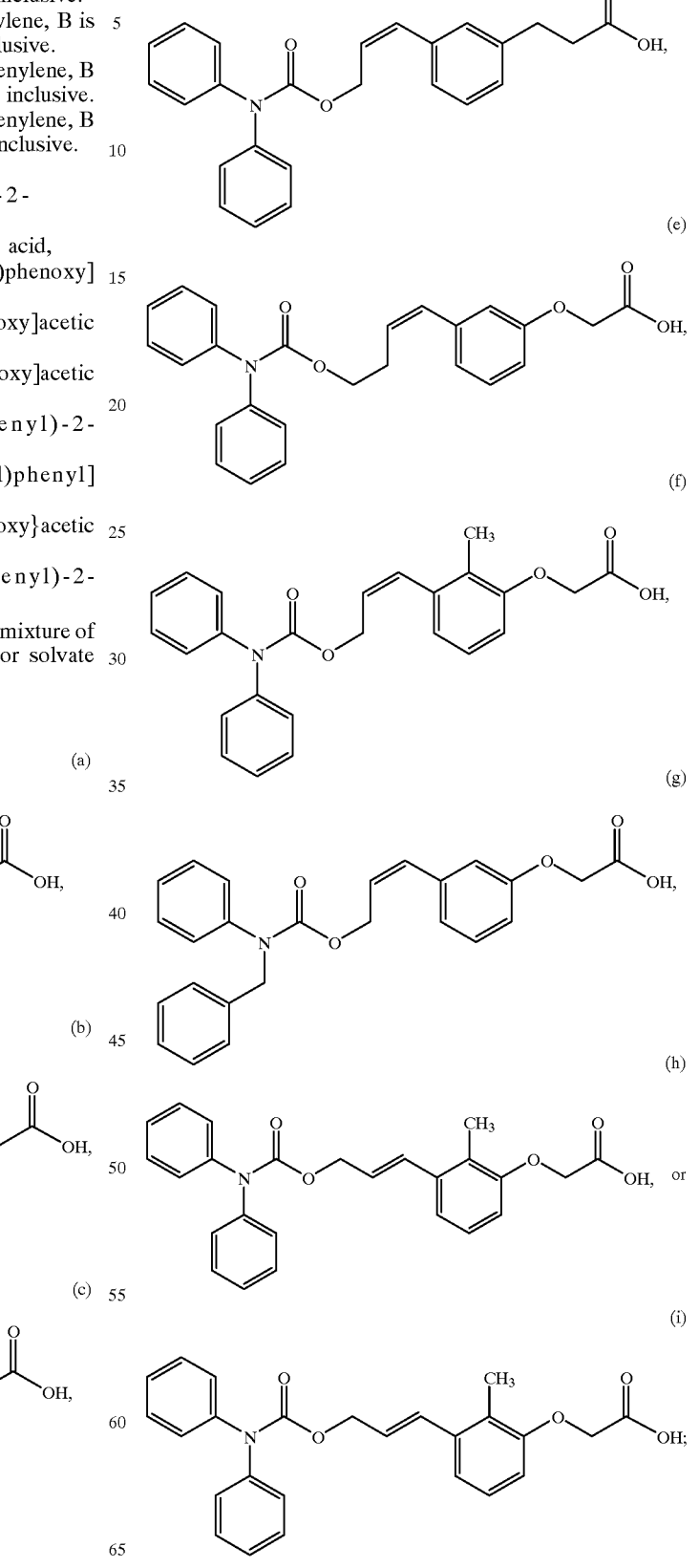

or an individual isomer, a racemic or non-racemic mixture of isomers, or a pharmaceutically acceptable salt or solvate thereof.

14. A pharmaceutical composition comprising a therapeutically effective amount of at least one compound of claim 1 in admixture with at least one pharmaceutically acceptable carrier.

15. The pharmaceutical composition of claim 14 wherein the at least one compound is suitable for administration to a subject having a disease state that is alleviated by treatment with an IP receptor modulator.

16. The pharmaceutical composition of claim 15 wherein the IP receptor modulator is an IP receptor agonist.

17. A pharmaceutical composition suitable for administration to a subject comprising a therapeutically effective amount of at least one compound of claim 1 in admixture with at least one pharmaceutically acceptable carrier.

18. A method of treatment comprising administering to a subject in need of such treatment, a therapeutically effective amount of at least one compound of claim 1.

19. The method of claim 18 wherein the subject has a disease state associated with improper wound healing, tissue necrosis, premature uterine contraction, gastric ulceration, sexual dysfunction in males and females, severe menstrual pain, improper immunoregulation, improper platelet aggregation, or improper neutrophil function.

20. The method of claim 18 wherein the compound is an IP receptor modulator.

21. The method of claim 20 wherein the IP receptor modulator is an IP receptor agonist.

22. A method of treatment comprising administering to a subject suffering from a disease state associated with improper blood flow, a therapeutically effective amount of at least one compound of claim 1.

23. The method of claim 22 wherein the disease state associated with improper blood flow is a cardiovascular disease state.

24. The method of claim 23 wherein the cardiovascular disease state is peripheral arterial occlusive disease (PAOD), intermittent claudication, critical limb ischemia, thrombotic disease, atherosclerosis, thromboangiitis obliterans (Buerger's disease), Raynaud's syndrome, Takayashu's disease, migratory superficial vein thrombophlebitis, acute arterial occlusion, coronary artery disease, restenosis following angioplasty, stroke, or recurrent myocardial infarction.

25. The method of claim 22 wherein the disease state associated with improper blood flow is a hypertensive disease state.

26. The method of claim 25 wherein the hypertensive disease state is pulmonary hypertension, occular hypertension, or tinnitus associated with hypertension.

27. The method of claim 22 wherein disease state associated with improper blood flow is an ischemia disease state.

28. The method of claim 27 wherein the ischemia disease state is ischemia associated with an allograft transplantation.

29. The method of claim 22 wherein the disease state associated with improper blood flow is a renal disease state.

30. The method of claim 29 wherein the renal disease state is renal failure, improper diuresis, improper natriuresis, or improper kaliuresis.

31. The method of claim 22 wherein the compound is an IP receptor modulator.

32. The method of claim 31 wherein the IP receptor modulator is an IP receptor agonist.

* * * * *